(12) United States Patent
Chen et al.

(10) Patent No.: US 8,772,460 B2
(45) Date of Patent: Jul. 8, 2014

(54) THERMOSTABLE FGF-2 MUTANT HAVING ENHANCED STABILITY

(71) Applicant: Wisconsin Alumni Research Foundation, Madison, WI (US)

(72) Inventors: Guokai Chen, Rockville, MD (US); James A. Thomson, Madison, WI (US); Zhonggang Hou, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/717,275

(22) Filed: Dec. 17, 2012

(65) Prior Publication Data

US 2013/0236959 A1 Sep. 12, 2013

Related U.S. Application Data

(60) Provisional application No. 61/576,824, filed on Dec. 16, 2011.

(51) Int. Cl.
| | | |
|---|---|---|
| *C12N 5/00* | (2006.01) | |
| *C07H 21/04* | (2006.01) | |
| *C07K 16/00* | (2006.01) | |
| *C12N 5/0735* | (2010.01) | |
| *C12N 5/074* | (2010.01) | |
| *C12N 5/071* | (2010.01) | |

(52) U.S. Cl.
CPC .......... *C12N 5/0606* (2013.01); *C12N 5/0607* (2013.01); *C12N 5/0696* (2013.01); *C12N 2501/115* (2013.01)
USPC .......... 530/399; 435/375; 435/402; 435/405; 536/23.51

(58) Field of Classification Search
CPC .......... C07K 14/50; C12N 2501/115
See application file for complete search history.

(56) References Cited

U.S. PATENT DOCUMENTS

| | | | |
|---|---|---|---|
| 7,186,526 B2 | 3/2007 | Fiddes et al. | |
| 7,659,379 B1 | 2/2010 | Blaber et al. | |
| 8,158,424 B2 | 4/2012 | Thomson et al. | |
| 2012/0178166 A1 | 7/2012 | Chen et al. | |
| 2012/0202291 A1 | 8/2012 | Chen et al. | |

OTHER PUBLICATIONS

Levenstein et al (2008), "Secreted proteoglycans directly mediate human embryonic stem cell-basic fibroblast growth factor 2 interactions critical for proliferation," Stem Cells, Dec;26(12):3099-3107. Epub Sep. 18, 2008.
Beenken et al (2009), "The FGF family: biology, pathophysiology and therapy," Nat Rev Drug Discov, Mar;8 (3):235-53. doi: 10.1038/nrd2792.
Zhang et al (2006), "Receptor specificity of the fibroblast growth factor family. The complete mammalian FGF family," J Biol Chem, Jun. 9;281(23):15694-15700. Epub Apr. 4, 2006.
Mohammadi et al (2005), "Structural basis for fibroblast growth factor receptor activation," Cytokine Growth Factor Rev., Apr;16(2):107-137.
Eswarakumar et al (2005), "Cellular signaling by fibroblast growth factor receptors," Cytokine Growth Factor Rev. Apr;16(2):139-149. Epub Feb. 1.
Itoh et al (2004), "Evolution of the Fgf and Fgfr gene families," Trends Genet, Nov;20(11):563-569.
Ornitz et al (2001), "Fibroblast growth factors," (3):REVIEWS3005. Epub Mar. 9, 2001.
Vallier et al. (2005), "Activin/Nodal and FGF pathways cooperate to maintain pluripotency of human embryonic stem cells," J Cell Sci., Oct. 1;118(Pt 19):4495-4509.
Xu et al (2005), "Basic FGF and suppression of BMP signaling sustain undifferentiated proliferation of human ES cells," Nature Methods, Mar;2(3):185-190.
Lanner et al (2010), "The role of FGF/Erk signaling in pluripotent cells," Development, Oct;137(20):3351-3360.
Eiselleova et al (2009), "A complex role FGF-2 in self-renewal, survival, and adhesion of human embryonic stem cells," Stem Cells, Aug;27(8):1847-1857.
Chen, G. et al., "Chemically defined conditions for human iPS cell derivation and culture", Nat. Methods, 2011, vol. 8, No. 5, pp. 424-429.
Furue et al. (2008), "Heparin promotes the growth of human embryonic stem cells in a defined serum-free medium," Proc Natl Acad Sci U S A., Sep. 9, 105(36):13409-14. doi: 10.1073/pnas.0806136105. Epub Aug. 25, 2008.
Schlessinger et al., "Crystal Structure of a Ternary FGF-FGFR-Heparin Complex Reveals a Dual Role for Heparin in FGFR Binding and Dimerization", Mol. Cell., 2000, vol. 6, pp. 743-750.
Ludwig, T.E. et al., "Feeder-independent culture of human embryonic stem cells", Nature Methods, 2006, vol. 3, No. 8, pp. 637-646.
Zamai, M. et al., "Nature of Interaction between Basic Fibroblast Growth Factor and the Antiangiogenic Drug 7,7-(Carbonyl-Bis[Imino-N-Methyl-4,2-Pyrrolecarbonylimino[N-Methyl-4,2-Pyrrole]-Carbonylimino])-Bis-(1,3-Naphtalene Disulfonate). II. Removal of Polar Interactions Affects Protein Folding", Biophysical Journal, 2002, vol. 82, pp. 2652-2664.
Amit, M. et al.,"Feeder layer- and serum-free culture of human embryonic stem cells", 2004, Biol. Reproduction, vol. 70, pp. 837-845.
Ludwig, T.E. et al.,"Derivation of human embryonic stem cells in defined conditions", 2006, Nat. Biotechnol., vol. 24, pp. 185-187.
Chen et al., "Thermal stability of fibroblast growth factor protein is a determinant factor in regulating self-renewal Differentiation, and reprogramming in human pluripotent stem cells", 2012, Stem Cells, vol. 30 , No. 4, pp. 623-630.
Wang, L. et al., "Self-renewal of human embryonic stem cells requires insulin-like growth factor-1 receptor and ERBB2 receptor signaling", 2007, Blood, vol. 110, No. 12, pp. 4111-4119.
Bendall, S.C. et al., "IGF and FGF cooperatively establish the regulatory stem cell niche of pluripotent human cells in vitro", 2007, Nature, vol. 448, No. 7157, pp. 1015-1021.
Chen et al., "Actin-Myosin Contractility Is Responsible for the Reduced Viability of Dissociated Human Embryonic Stem Cells", 2010, Cell Stem Cell, vol. 7, No. 2, pp. 240-248.

(Continued)

*Primary Examiner* — Deborah Crouch
*Assistant Examiner* — Titilayo Moloye
(74) *Attorney, Agent, or Firm* — Quarles & Brady LLP

(57) ABSTRACT

Thermostable FGF-2 proteins having enhanced ability to support human pluripotent stem cell cultures are provided. Also provided are methods and compositions utilizing thermostable FGF-2 proteins.

26 Claims, 18 Drawing Sheets

(56) References Cited

OTHER PUBLICATIONS

Kim, J. et al., "Identification of a Key Structural Element for Protein Folding Within β-Hairpin Turns", 2003, J. Mol. Biol., vol. 328, No. 4, pp. 951-961.

Byrch, S.R. et al., "Symmetric Primary and Tertiary Structure Mutations within a Symmetric Superfold: A Solution, not a Constraint, to Achieve a Foldable Polypeptide", 2004, J. Mol. Biol., vol. 344, No. 3, pp. 769-780.

Lee, J. et al., "The Interaction between Thermodynamic Stability and Buried Free Cysteines in Regulating the Functional Half-Life of Fibroblast Growth Factor-1", 2009, J. Mol. Biol., vol. 393, No. 1, pp. 113-127.

Zakrzewska, M. et al., "Highly Stable Mutants of Human Fibroblast Growth Factor-1 Exhibit Prolonged Biological Action", 2005, J. Mol. Biol., vol. 352, No. 4, pp. 860-875.

Zakrzewska, M. et al., "Design of fully active FGF-1 variants with increased stability", 2004, Protein Eng. Des. Sel., vol. 17, No. 8, pp. 603-611.

Zakrzewska, M. et al., "Increased Protein Stability of FGF1 Can Compensate for Its Reduced Affinity for Heparin", 2009, J. Biol. Chem., vol. 284, No. 37, pp. 25388-25403.

Wiedlocha et al., "Stimulation of Proliferation of a Human Osteosarcoma Cell Line by Exogenous Acidic Fibroblast Growth Factor Requires both Activation of Receptor Tyrosine Kinase and Growth Factor Internalization", 1996, Mol. Cell. Biol., vol. 16, No. 1, pp. 270-280.

Sato et al., "Maintenance of pluripotency in human and mouse embryonic stem cells through activation of Wnt signaling by a pharmacological GSK-3-specific inhibitor", 2004, Nat. Med., vol. 10, No. 1, pp. 55-63.

Eswarakumar et al. (2005), "Cellular signaling by fibroblast growth factor receptors," Cytokine Growth Factor Rev. Apr;16(2):139-149. Epub Feb. 1.

Vallier et al (2005), "Activin/Nodal and FGF pathways cooperate to maintain pluripotency of human embryonic stem cells," J Cell Sci., Oct. 1;118(Pt 19):4495-4509.

Xu et al. (2005), "Basic FGF and suppression of BMP signaling sustain undifferentiated proliferation of human ES cells," Nature Methods, Mar;2(3):185-190.

Eiselleova et al (2009), "A complex role for FGF-2 in self-renewal, survival, and adhesion of human embryonic stem cells," Stem Cells, Aug;27(8):1847-1857.

Furue et al (2008), "Heparin promotes the growth of human embryonic stem cells in a defined serum-free medium," Proc Natl Acad Sci U S A., Sep. 9;105(36):13409-14. doi: 10.1073/pnas.0806136105. Epub Aug. 25, 2008.

Zamai, M. et al., "Nature of Interaction between Basic Fibroblast Growth Factor and the Antiangiogenic Drug 7,7-(Carbonyl-Bis[Imino-N-Methyl-4,2-Pyrrolecarbonylimino[N-Methl-4,2-pyrrole]-Carbonylimino])-Bis-(1,3-Naphtalene Disulfonate). II. Removal of Polar Interactions Affects Protein Folding", Biophysical Journal, 2002, vol. 82, pp. 2652-2664.

Amit, M. et al., "Feeder layer- and serum-free culture of human embryonic stem cells", 2004, Biol. Reproduction, vol. 70, pp. 837-845.

Chen et al., "Thermal stability of fibroblast growth factor protein is a determinant factor in regulating self-renewal, Differentiation, and reprogramming in human pluripotent stem cells", 2012, Stem Cells, vol. 30 , No. 4, pp. 623-630.

Wang, L. et al., "Self-renewal of human embryonic stem cells requires insulin-like growth factor-1 receptor and ERBB2 receptor signaling ", 2007, Blood, vol. 110, No. 12, pp. 4111-4119.

| P5 - TeSR | | | | |
|---|---|---|---|---|
| Condition | Oct4 | Tra181 | SSEA4 | Pass/Fail |
| Control | 98.4 | 93.0 | 98.6 | P |
| 10ng/mL FGF-2 K128D | 93.3 | 86.1 | 78.5 | F |
| 30ng/mL FGF-2 K128D | 82.9 | 60.5 | 67.4 | F |
| 50ng/mL FGF-2 K128D | 95.2 | 81.9 | 78.5 | F |
| 100ng/mL FGF-2 K128D | 93.6 | 80.5 | 83.0 | P |

| P5 – E8 | | | | |
|---|---|---|---|---|
| Condition | Oct4 | Tra181 | SSEA4 | Pass/Fail |
| Control | 98.7 | 89.0 | 85.3 | P |
| 10ng/mL FGF-2 K128D | 87.1 | 74.9 | 76.7 | F |
| 30ng/mL FGF-2 K128D | 95.1 | 82.6 | 69.9 | F |
| 50ng/mL FGF-2 K128D | 97.1 | 83.7 | 78.9 | F |
| 100ng/mL FGF-2 K128D | 97.7 | 85.6 | 86.4 | P |

B.

| P5 - Cell Line #1 | | | | |
|---|---|---|---|---|
| Condition | Oct4 | Tra181 | SSEA4 | Pass/Fail |
| TeSR Control | 99.6 | 94.7 | 99.2 | P |
| TeSR + 30ng/mL FGF-2 K128D | 97.0 | 80.3 | 91.3 | P |
| E8 Control | 99.1 | 68.4 | 89.3 | F |
| E8 + 30ng/mL FGF-2 K128D | 90.4 | 41.6 | 60.3 | F |

| P5 - Cell Line #2 | | | | |
|---|---|---|---|---|
| Condition | Oct4 | Tra181 | SSEA4 | Pass/Fail |

| | | | | |
|---|---|---|---|---|
| TeSR Control | 99.9 | 96.5 | 99.9 | P |
| TeSR + 30ng/mL FGF-2 K128D | 95.5 | 92.9 | 96.3 | P |
| E8 Control | 90.6 | 88.7 | 91.0 | P |
| E8 + 30ng/mL FGF-2 K128D | 62.0 | 31.5 | 60.8 | F |

FIG. 11C

| P5 – Cell Line #1 | | | | |
|---|---|---|---|---|
| Condition | Oct4 | Tra181 | SSEA4 | Pass/Fail |
| TeSR Control | 93.8 | 95.6 | 97.6 | P |
| TeSR + 5ng/mL FGF-2 K128N | 98.7 | 96.5 | 97.6 | P |
| TeSR + 15ng/mL FGF-2 K128N | 98.3 | 96.3 | 96.7 | P |
| TeSR + 30ng/mL FGF-2 K128N | 95.4 | 88.2 | 91.4 | P |

| P5 – Cell Line #1 | | | | |
|---|---|---|---|---|
| Condition | Oct4 | Tra181 | SSEA4 | Pass/Fail |
| E8 Control | 98.7 | 95.9 | 97.4 | P |
| E8 + 5ng/mL FGF-2 K128N | 78.7 | 34.0 | 90.4 | F |
| E8 + 15ng/mL FGF-2 K128N | 92.7 | 70.2 | 84.4 | F |
| E8 + 30ng/mL FGF-2 K128N | 92.2 | 80.9 | 88.2 | P |

```
                           SEQUENCE LISTING

<160> NUMBER OF SEQ ID NOS: 4

<210> SEQ ID NO 1
<211> LENGTH: 155
<212> TYPE: PRT
<213> ORGANISM: Homo sapiens

<400> SEQUENCE: 1

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 2
<211> LENGTH: 155
<212> TYPE: PRT
<213> ORGANISM: Artificial Sequence
<220> FEATURE:
<223> OTHER INFORMATION: Amino acid sequence of FGF-2 K128N

<400> SEQUENCE: 2

Met Ala Ala Gly Ser Ile Thr Thr Leu Pro Ala Leu Pro Glu Asp Gly
1               5                   10                  15
```

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
                35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Asn
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 3
<211> LENGTH: 155
<212> TYPE: PRT
<213> ORGANISM: Artificial Sequence
<220> FEATURE:
<223> OTHER INFORMATION: Amino acid sequence of FGF-2 K128D relative to
      wild type FGF-2

<400> SEQUENCE: 3

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
                35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Asp
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 4
<211> LENGTH: 465
<212> TYPE: DNA
<213> ORGANISM: Artificial Sequence
<220> FEATURE:
<223> OTHER INFORMATION: Nucleic acid sequence encoding the amino acid
      sequence shown for SEQ ID NO:2.

<400> SEQUENCE: 4

-continued

```
atggcggcgg gcagcattac caccctgccg gcgctgccgg aagatggcgg cagcggcgcg        60
tttccgccgg gccattttaa agatccgaaa cgcctgtatt gcaaaaacgg cggcttttt        120 ctgcgcattc atccggatgg ccgcgtggat ggcgtgcgcg aaaaaagcga tccgcatatt      180
aaactgcagc tgcaggcgga agaacgcggc gtggtgagca ttaaaggcgt gtgcgcgaac      240
cgctatctgg cgatgaaaga agatggccgc ctgctggcga gcaaatgcgt gaccgatgaa      300 tgctttttt ttgaacgcct ggaaagcaac aactataaca cctatcgcag ccgcaaatat        360
accagctggt atgtggcgct gaaccgcacc ggccagtata aactgggcag caaaaccggc      420
ccgggccaga aagcgattct gtttctgccg atgagcgcga aaagc                     465
```

THERMOSTABLE FGF-2 MUTANT HAVING ENHANCED STABILITY

CROSS-REFERENCE TO RELATED APPLICATIONS

This application claims priority to U.S. Provisional Patent Application No. 61/576,824 filed Dec. 16, 2011, which is incorporated by reference herein in its entirety.

STATEMENT REGARDING FEDERALLY SPONSORED RESEARCH OR DEVELOPMENT

This invention was made with government support under ES017166 and GM081629 awarded by the National Institutes of Health. The government has certain rights in the invention.

BACKGROUND

The invention relates generally to methods and compositions for culturing human pluripotent stem cells, and, more particularly, to methods and compositions having thermostable fibroblast growth factor (FGF) proteins for improved culture efficiency.

Human pluripotent cells, such as human embryonic stem (ES) cells and human induced human pluripotent stem (iPS) cells have the potential to proliferate indefinitely and to differentiate into cells of all three germ layers (Lowry et al., PNAS 105: 2883-2888, 2008; Park et al., Nature 451:141-U141, 2008; Reubinoff et al., Nat. Biotechnol. 18:399-404, 2000; Takahashi et al., Cell 131:861,872, 2007; Thomson et al., Science 282:1145-1147, 1998; Yu et al., Science 318: 1917-1920, 2007). These properties make human pluripotent cells invaluable for studying embryogenesis, for drug discovery, and for clinical applications.

Current in vitro culture methods for human ES and iPS cells require the addition of exogenous growth factors (Amit et al., Nat. Rev. Drug Discov. 8:235-253, 2004; Ludwig et al., Nat. Biotechnol. 24:185-187, 2006; Sato et al., Nat. Med. 10:55-63, 2004; Vallier et al., J. Cell Sci. 118:4495-4509, 2005; Wang et al., Blood 110:4111-4119, 2007). It is presently thought that three growth factors are sufficient to maintain pluripotency and self-renewal of human ES and iPS cells through activation of the FGF, TGF/Nodal, and Insulin/IGF pathways (Bendall et al., Nature 448:1015-1021 (2007); Eiselleova et al., Stem Cells 27:1847-1857 (2009); Vallier et al., J. Cell Sci. 118:4495-4509 (2005)).

The FGF pathway has been implicated in many stages of human pluripotent cell regulation, cell survival, proliferation, pluripotency, and lineage determination during differentiation (Eiselleova et al., Stem Cells 27:1847-1857, 2009; Lanner and Rossant, Development 137:3351-3360, 2010; Levenstein et al., Stem Cells 24:568-574, 2006; Vallier et al., J. Cell Sci. 118:4495-4509, 2005; Xu et al., Nat. Meth. 2:185-190, 2005). The FGF pathway is activated through the binding of FGF proteins to FGF receptors, which triggers MAP kinase cascades to regulate downstream events (Lanner and Rossant, 2010).

FGF-1-9 are 150-250 amino acid proteins with approximately 30-70% sequence homology in their 120-amino acid core region (Ornitz et al., Genome Biol. 2:3005.1-3005.12 (2001); Itoh et al., Trends Genet. 20:563-569 (2004)). Because of their substantial sequence homology, new members of the FGF family were identified in several species, from *Caenorhabditis elegans* to *Homo sapiens* (Itoh et al.), using homology-based methods. Twenty-two FGF family members have been identified in humans and mice (Ornitz et al., 2001; Itoh et al., 2004).

While different FGF proteins are used for various applications in cell culture, qualitative differences in cell responses elicited by the various FGF proteins remain ill-defined and poorly understood. The functional difference between FGF proteins that can and cannot support human pluripotent stem cells might be attributable to (1) the different affinity of the various FGF proteins to each of the four FGF receptors (FGFR) that lead to the activation of specific pathways (Eswarakumar et al., Cytokine Growth Factor Rev. 16:139-149, 2005; Mohammadi et al., Cytokine Growth Factor Rev. 16:107-137, 2005; Zhang et al., J. Biol. Chem. 281:15694-15700, 2006); and (2) the differential expression of FGFs and FGFRs in specific tissues (Beenken and Mohammadi, Nat. Rev. Drug Discov. 8:235-253, 2009). However, these factors insufficiently explain the functional differences between FGF-2 and other FGF proteins in human ES cell culture.

FGF-2 is routinely used for human ES and iPS cell culture (Levenstein et al., Stem Cells 24:568-574, 2006). Interestingly, FGF-1 did not support hESC pluripotency or cell survival, even though FGF-1 targets the same set of receptors as FGF-2 (Zhang et al., J. Biol. Chem. 281:15694-15700, 2006).

While FGF-2 supports pluripotency in defined long-term human pluripotent cell cultures, high FGF-2 concentrations (e.g., 100 ng/ml) are required, which significantly increases culture cost. It has been suggested that high FGF-2 concentrations might be required to satisfy specific dose-dependent signaling thresholds, and to overcome obstacles such as protein degradation (Levenstein et al., Stem Cells 24:568-574, 2006). Heparin and heparan sulfate can facilitate binding between FGF and FGFR to stimulate downstream activation (Levenstein et al., Stem Cells 26:3099-3107, 2008; Mohammadi et al., Curr. Opin. Struct. Biol. 15:506-516, 2005). Heparin and heparan sulfate promote pluripotency (Fume et al., PNAS 105:13409-13414, 2008; Levenstein et al., Stem Cells 26:3099-3107, 2008), although it is unclear whether they do so via the FGF pathway. Heparin appears to increase the stability of FGF-1 and might be important in the formation of FGF-1-FGFR complexes (Zakrzewska et al., J. Biol. Chem. 284:25388-25403 (2009)). While FGF-2 from zebrafish is capable of supporting self-renewal (Ludwig et al., Nat. Meth. 3:637-646, 2006), effective mammalian FGFs that can be used as an alternative to mammalian wild type FGF-2 are desirable.

There is a need in the art for more efficient growth factors that can support human pluripotent stem cells in culture.

BRIEF SUMMARY

In a first aspect, the present invention is summarized as an isolated fibroblast growth factor-two (FGF-2) polypeptide (SEQ ID NO:2) that differs from wild type FGF-2 (SEQ ID NO: 1) at amino acid position 128, wherein the difference is a K128N substitution.

In some embodiments disclosed herein a nucleic acid is provided that encodes the above-mentioned FGF-2 having a K128N substitution (SEQ ID NO:2). Also disclosed herein is a genetically modified cell (e.g., a genetically modified mammalian cell) expressing the above-mentioned FGF-2 (SEQ ID NO:1) having a K128N substitution (SEQ ID NO:2).

In a second aspect, the present invention is summarized as a method for culturing human pluripotent stem cells, the method comprising the step of culturing a human pluripotent stem cell in a medium comprising a K128-substituted thermostable fibroblast growth factor-two (FGF-2), (SEQ ID NO:2) that differs from wild type FGF-2 (SEQ ID NO: 1) at position 128 of the wild type FGF-2, wherein the difference is a K128N substitution.

In some embodiments of the second aspect, the human pluripotent stem cells to be cultured are human embryonic stem cells. In other embodiments the human pluripotent stem cells to be cultured are human induced human pluripotent stem cells.

In some embodiments of the second aspect, the culture medium to be used further includes heparin.

In some embodiments of the second aspect, the concentration of thermostable FGF-2 to be used is less than 40 ng/ml. In other embodiments, the concentration of thermostable FGF-2 to be used is less than 10 ng/ml. In other embodiments, the concentration of thermostable FGF-2 to be used is less than 3 ng/ml. In other embodiments, the concentration of thermostable FGF-2 to be used is less than 1 ng/ml.

In some embodiments of the second aspect, the human pluripotent cells are human embryonic stem cells or human induced human pluripotent stem cells.

In a third aspect, the present invention is summarized as a fully-defined medium suitable for culturing human pluripotent cells in an undifferentiated state comprising thermostable fibroblast growth factor-two (FGF-2) K128N sequence variant (SEQ ID NO:2) that differs from wild type FGF-2 (SEQ ID NO: 1) at amino acid 128 of the wild type FGF-2, wherein the difference is a K128N substitution.

In some embodiments of the third aspect, the concentration of thermostable FGF-2 in the fully defined medium is less than 40 ng/ml. In other embodiments, the concentration of thermostable FGF-2 in the fully defined medium is less than 10 ng/ml. In other embodiments, the concentration of thermostable FGF-2 in the fully defined medium is less than 3 ng/ml. In other embodiments, the concentration of thermostable FGF-2 in the fully defined medium is less than 1 ng/ml.

In a fourth aspect, the present invention is summarized as a composition that contains a human pluripotent stem cell, a medium suitable for culturing human pluripotent cells in an undifferentiated state, and a thermostable FGF-2 that differs from wild type FGF-2 (SEQ ID NO: 1) at amino acid 128 of the wild type FGF-2, wherein the difference is a K128N substitution.

In some embodiments of the fourth aspect the concentration of thermostable FGF-2 in the composition is less than 40 ng/ml. In other embodiments, the concentration of thermostable FGF-2 in the composition is less than 10 ng/ml. In other embodiments, the concentration of thermostable FGF-2 in the composition is less than 3 ng/ml. In other embodiments, the concentration of thermostable FGF-2 in the composition is less than 1 ng/ml.

In a fifth aspect, the present invention is summarized as a method for reprogramming a somatic cell into a cell of higher potency, including the steps of culturing the human pluripotent stem cell in a medium containing a thermostable FGF-2 until the cell expresses markers indicative of a higher potency cell, wherein the thermostable FGF-2 differs from wild type FGF-2 (SEQ ID NO: 1) at amino acid 128 of the wild type FGF-2 in having a K128N substitution. In some embodiments of the fifth aspect, the medium to be used consists essentially of water, salts, amino acids, vitamins, a carbon source, insulin, selenium, and the thermostable FGF-2.

The methods and compositions described herein are useful in a variety of applications, such as maintaining and passaging a viable population of human pluripotent stem cells, or reprogramming human somatic cells into pluripotent stem cells.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to preclude the invention from covering all modifications, equivalents and alternatives. Reference should therefore be made to the claims recited herein for interpreting the scope of the invention.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 1A shows that ERK phosphorylation correlates with the activation of FGF receptors in human ES cells. H1 cells were incubated in E8 medium (Chen et al., Nat. Meth. 8:424-429, 2011) (100 ng/ml FGF-2 and 2 ng/ml Tgfβ) for 30 minutes with drug treatments (10 μM SU5402—FGFR inhibitor or 10 μM SB43542—TGFβ inhibitor, or both). Proteins were harvested to analyze ERK1/2 phosphorylation (pERK1/2) by western blot. FIG. 1B shows that inhibition of ERK phosphorylation suppresses NANOG expression; NANOG expression was measured after three days of incubation. FIG. 1C shows screening for FGFs supporting sustained ERK phosphorylation. H1human ES cells were plated into basic medium ($E_8$ media without TGFβ) with different FGFs (100 ng/ml) for 24 hours, and proteins were then collected to detect ERK phosphorylation. FIG. 1D shows screening for FGFs supporting pluripotency. H1 cells were maintained in the same medium as (C) for three days, cells were harvested to measure the expression of NANOG by RT-qPCR. GAPHD was used as control. FIG. 1E shows screening for FGFs that stimulate ERK phosphorylation in short exposure. Media used in (C) were applied for 15 minutes on FGF-starved human ES cells before proteins were collected to analyze for ERK phosphorylation. FIG. 1F shows how thermostability of FGF affects activation of ERK phosphorylation. Media used in (C) were incubated at 37° C. for 6 hours, and then applied for 15 minutes on FGF-starved human ES cells, before proteins were collected for ERK phosphorylation analysis.

FIG. 2A shows that ERK phosphorylation decreases after initial activation. FGF-2 (100 ng/ml) was added to FGF-starved human ES cells, and proteins were collected at specific time points for western blot. ERK phosphorylation was significantly lower than previous time points. FIG. 2B shows that there was no significant loss of FGF-2 activity in media at 12 hours. Growth media were collected from the cell culture and applied to FGF-starved cells for 15 minutes and proteins were collected for western blot. FIG. 2C shows that ERK phosphorylation is controlled at a consistently moderate level in continuous FGF culture. FGF-2 was applied onto FGF-starved and FGF-primed cells, and cells were harvested at specific time points.

FIG. 3A shows FGF18 has weaker capacity to induce ERK phosphorylation compared to FGF-2. FGF18 and FGF-2 (10 ng/ml) were applied on FGF-starved human ES cells for 15 minutes, and protein was harvested to detect ERK phosphorylation by western blot. FIG. 3B shows dosage dependent ERK phosphorylation by FGF-2. A series of human and zebrafish FGF-2 was applied on FGF-starved human ES cells for 15 minutes and protein was harvested to detect ERK phosphorylation by western blot. Human and zebrafish FGF-2 have similar capacity for activating ERK phosphorylation. FIG. 3C shows that heparin maintained zebrafish FGF-2 during 37° C. (versus 4 C) incubation. FGF-2 was treated with various conditions before it was applied on FGF-starved human ES cells for 15 minutes, and protein was harvested to detect ERK phosphorylation by western blot. Heparin maintained FGF-2 activity, while BSA and β-mecaptoethanol could not. FIGS. 3D and 3E show that additional reagents can maintain FGF-2 stability. Human FGF-2 was treated with various reagents at 37° C. for 24 hours and was then applied to FGF-starved cells for ERK phosphorylation detection. Dextran Sulfate and Cyclodextrin Sulfate also helped maintain FGF activity. FIG. 3F shows that heparin must be present during incubation to maintain FGF-2 stability. Zebrafish FGF-2 was treated under various conditions at 37° C. for 24 hours, and then applied on FGF-starved human ES cells for 15 minutes, and protein was harvested to detect ERK phosphorylation by western blot. In treatment 4, FGF-2 medium was incubated at 37° C. without heparin, and medium was then mixed with heparin to treat cells; in treatment 5, FGF-2 medium contained heparin during 37° C. treatment. FIG. 3G shows that heparin prevents loss of zebrafish FGF-2 monomer/dimer. Zebrafish FGF-2 (50 µg/ml) was treated under various conditions, then separated on PAGE-gel, and stained with coomassie blue. DTT was added into samples to demonstrate that same amount of total FGF-2 was used in the treatment. Heparin increased FGF-2 dimers, but the total amount of dimer and monomer was not changed after 37° C. treatment. In control and BME treatment, most of monomer was lost after 37° C. treatment, and protein aggregates were observed in corresponding wells.

FIG. 4A shows FGF-2 losing activity after 24-hour incubation at 37° C. Media with FGF-2 were incubated at 37° C. and then applied for 15 minutes on FGF-starved human ES cells before proteins were collected to analyze for ERK phosphorylation. FIG. 4B shows heparin helping to maintain FGF-2 activity. Heparin was co-incubated with FGF-2, and then applied for 15 minutes on FGF-starved human ES cells at specific time points. FIG. 4C shows human FGF-2 aggregates after incubation at 37° C. Human FGF-2 (100 ng/ml) was incubated at 37° C. or 4° C. for 24 hours, separated by PAGE gel, and detected by anti-FGF-2 western blot. FIG. 4D shows heparin enhancing NANOG expression. H1 cells were cultured with heparin for 5 days, and RNA was collected to analyze NANOG expression.

FIG. 7A shows the location of K128N relative to FGF-2 wild type. FIG. 7B shows that mutating that FGF-2 heparin binding-site (K128N) stabilized FGF-2 proteins during 37° C. treatment.

FIG. 9A shows that the level of pluripotency marker Nanog is significantly higher in FGF-2 K128N culture and differentiation markers (HAND1 and GATA2) are lower in FGF-2 K128N culture each relative to cells cultured with wild type FGF-2. FIG. 9B shows karyotyping of H1 hES cells cultured with FGF-2 K128N at 1 ng/ml. The chromosomal profile of the cells was 46, XY, no clonal abnormalities were detected. FIG. 9C shows Nanog expression levels in hES cells cultured with FGF-2 K128N in the presence or absence of BSA.

FIG. 11A-C illustrates that FGF-2 K128D does not support pluripotency at lower concentrations than wild type FGF-2. Conditions were assayed by flow cytometry for the pluripotency markers Oct4, Tra181 and SSEA4 at P0 and P5. Criteria for "human pluripotent" is >90% Oct4 expression and >80% Tra181 and SSEA4 expression. 100 ng/mL zebrafish bFGF as a control. FIG. 11A depicts two tables showing that FGF-2 K128D does not support pluripotency at 10-, 30- or 50 ng/ml in either TeSR (upper) or E8 (lower) medium. FIG. 11B depicts two tables showing that FGF-2 K128D manufactured by Aldevron supports pluripotency of two hiPSC lines for five passages in TeSR, but does not support pluripotency of the same two cell lines passaged in E8, at 30 ng/mL. FIG. 11C depicts two tables showing that FGF-2 K128N supports pluripotency at 30 ng/ml in either TeSR or E8 medium.

DETAILED DESCRIPTION

Figure 1A:
FIG. 1A-F illustrates that thermostability of FGF affects its ability to stimulate ERK phosphorylation.

The invention relates to an FGF-2 variant having enhanced thermostability, and its application to compositions and methods directed to the growth or generation of human pluripotent stem cells.

The present invention relates to the inventors' observation that protein stability of FGF-family proteins plays an important role in determining the molecule's ability to support human pluripotent cell cultures. The invention provides a thermostable FGF-2 polypeptide, thermostable FGF-2 compositions, and methods to support human pluripotent stem cells in an undifferentiated state.

Many FGF-family members have repeatedly been shown to fail to maintain human pluripotent stem cells in culture for unknown reasons. In addition, relatively high concentrations of FGF-2 have typically been used to maintain human pluripotent stem cells in culture. The disclosure presented herein demonstrates, for the first time, that thermostability of FGF-2 can be a determining aspect of growth factor regulation in stem cell biology. The disclosure also demonstrates, for the first time, that certain changes in wild type FGF-2 result in a thermostable FGF-2 mutant having superior abilities, relative to wild type FGF-2, to maintain pluripotency at a given concentration in the long-term and under feeder independent conditions. Unexpectedly, the FGF-2 K128N mutant exhibits increased thermostability relative to wild type FGF-2, allowing for methods of culturing human pluripotent stem cells in the presence of lower levels of FGF-2 K128N relative to wild type FGF-2. The FGF-2 K128N mutant can also replace wild type FGF-2 in somatic cell reprogramming.

The inventors found that FGF-2 K128N is stable at 37° C. By "stable" it is meant that FGF-2 K128N retains biological activity following a 24 hour incubation at 37° C. in culture medium in the absence of heparain. For example, FGF-2 K128N can stimulate human ES cell ERK phosphorylation following 24 hours incubation at 37° C. In contrast, wild type FGF-2 is unable to stimulate human ES cell ERK phosphorylation following 24 hours incubation at 37° C.

Analogs of FGF-2 with reduced heparin binding are taught by Fiddes et al. (U.S. Pat. No. 7,186,526). However, FGF-2 K128N was not taught by Fiddes et al., nor is it obvious over Fiddes et al., at least because the predictions Fiddes et al. made regarding heparin binding affinity of FGF-2 analogs are incorrect. Fiddes et al. predicted that replacing basic (positive) amino acid residues thought to mediate heparin binding (i.e., amino acids at positions 23-27, 115-120, and 127-137 of wild type FGF-2) with neutral or negatively charged amino acids would result in a peptide with reduced or absent heparin binding. Fiddes et al. disclosed that in preferred substitutions in the predicted heparin binding domain of FGF-2 wherein positive amino acids (i.e., arginine (R), histidine (H) or lysine (K)) are substituted with negative amino acids (i.e., aspartic acid (D) and glutamic acid (E)). However, FGF-2 K128D (SEQ ID NO: 3) cannot maintain pluripotency of cells at levels lower that wild type FGF-2, suggesting that FGF-2 K128D does not exhibit increased stability relative to wildtype FGF-2 (FIGS. 11A and B and Example 6). FGF-2 K128N at 30 ng/ml was sufficient to support pluripotency of cells under the same conditions tested for FGF-2 K128D (FIG. 11C). It follows that a skilled artisan familiar with Fiddes et al. would not have predicted that replacing the positive amino acid lysine with the neutral amino acid asparagine at position 128 in wild type FGF-2 would increase stability of the resulting FGF-2 K128N relative to wild type FGF-2 because the predictions of Fiddes et al. were not upheld when tested experimentally.

I. Definitions

As used herein, "defined culture medium," "defined medium," or "fully defined medium" refers to an essentially serum-free medium that has known quantities of all ingredients.

As used herein, "enhanced ability to support pluripotency" means that a lower concentration of the thermostable FGF-2 can support pluripotency of human pluripotent cells in vitro, compared to the concentration of wild type FGF-2 that is known to support pluripotency. Thermostable FGF-2 can also support pluripotency of human pluripotent cells in vitro for a longer period of time (e.g., greater than 48 hours) compared to wildtype FGF-2, which is effective for less than 24 hours.

As used herein, "FGF-2," refers to an FGF-2 having an amino acid sequence with one or more sequence alterations, e.g., K128N, relative to wild type FGF-2 (SEQ ID NO: 1), and retaining the ability to stimulate ERK phosphorylation in human pluripotent stem cells after a 24 hour incubation period with a given amount of the thermostable FGF-2. For example, the thermostable FGF-2 may have a conservative substitution at K128, e.g., a K128N substitution as in SEQ ID NO:2. In preferred embodiments, FGF-2 K128N has the amino acid sequence of SEQ ID NO: 2.

As used herein, "iPS cells" refer to cells that are substantially genetically identical to their respective differentiated somatic cell of origin and display characteristics similar to human ES cells, as described herein. The cells can be obtained from various differentiated somatic cells, e.g., mononuclear blood cells, skin fibroblasts, keratinocytes, etc.

As used herein, "serum-free" means that neither the culture nor the culture medium contains serum or plasma, although purified or synthetic serum or plasma components (e.g., FGFs) can be provided in the culture in reproducible amounts as described below. For example, an essentially serum-free medium can contain less than about 1% serum or serum replacement.

As used herein "thermostable FGF-2" refers to an FGF-2 having enhanced thermostability relative to the respective wild type FGF amino acid sequence.

As used herein, "wild type amino acid sequence" refers to the most common amino acid sequence among members of a species.

II. Compositions

In some embodiments disclosed herein is an isolated thermostable FGF-2 polypeptide that includes the amino acid sequence of wild type FGF with at least one to about 5 amino acid changes, e.g., 1, 2, 3, 4, or 5 amino acid changes including, substitutions, deletions, additions, and combinations thereof. In some embodiments, the thermostable FGF-2 comprises an amino acid change in the heparin binding domain, as it was determined, as described herein, that the thermostable FGF-2 had enhanced stability relative to wildtype FGF-2, despite reduced binding of the thermostable FGF-2 to heparin. K128 is an amino acid that significantly contributes to heparin binding (Schlessinger et al., Mol. Cell. 6:743-750 (2000)). The skilled artisan would have found it counterintuitive to introduce a mutation in the heparin binding domain to increase thermostability of the molecule because binding of wildtype FGF-2 to heparin enhances its stability at 37° C. In some embodiments, the thermostable FGF-2 contains a substitution of the basic lysine residue at K128 of SEQ ID NO:1 (wild type FGF-2). In some embodiments, the basic lysine residue is substituted with a polar amino acid residue, i.e., asparagine, glutamine, threonine, or serine. In some embodiments, the K128 substitution is a K128N substitution, and the amino acid sequence of the thermostable FGF-2 is the amino acid sequence of SEQ ID NO:2. Also described herein are fusion polypeptides that include the amino acid sequence of a thermostable FGF-2. In some embodiments, the fusion polypeptide amino acid sequence includes a thermostable FGF-2 amino acid sequence corresponding to SEQ ID NO:1 with a polar amino acid substitution at K128. In some embodiments, the thermostable FGF-2 amino acid sequence corresponds to that of SEQ ID NO:2, which comprises a K128N substitution relative to wildtype FGF-2 (SEQ ID NO:1). Thermostable FGF-2 fusion polypeptides may include, an FGF-2 N-terminal or C-terminal fusion.

The disclosed thermostable FGF-2 polypeptides, have an enhanced ability compared to the wild type FGF-2 protein, to support pluripotency of cultured human pluripotent stem cells over time, such as several weeks or passages, in culture. For example, as described herein, human ES cells cultured with FGF-2 K128N retain pluripotency through at least six passages (i.e., approximately 25 days). Criteria for evaluating pluripotency of human pluripotent stem cells are known in the art, and include, for example, expression of Oct4 and Nanog mRNA and protein, and suppression of differentiation markers (e.g., Hand1 and Gata). The function of FGF-2 in human pluripotent stem cells can be conveniently assessed using a biochemical endpoint such as ERK phosphorylation. Measuring increased ERK phosphorylation in response to FGF stimulation, as described herein, provides a rapid measure of the ability of a thermostable FGF-2 to support in vitro pluripotency. Other methods of assessing pluripotency are also suitable.

Methods for introducing single or multiple changes into the amino acid sequence of an FGF protein are well known in the art (e.g., Kim et al. J. Mol. Biol. 328(4): 951-961 (2003); Brych et al. J. Mol. Biol. 344(3): 769-780 (2004); Lee et al., J. Mol. Biol. 393(1): 113-127 (2009); Zakrzewska et al., J. Mol. Biol. 352(4): 860-875 (2005); Zakrzewska et al., Protein Eng. Des. Sel. 17(8): 603-611 (2004); Zakrzewska et al., J. Biol. Chem. 284(37): 25388-25403 (2009); U.S. Pat. No. 7,659,379, each of which is incorporated herein by reference as if set forth in its entirety).

Also described herein are nucleic acids encoding any of the thermostable FGF-2 polypeptides described herein. As is well-known in the art, owing to the degeneracy of the genetic code, any combination of suitable codons may be used to code for a thermostable FGF-2 described herein. It will also be appreciated that codon choice may be optimized for expression of the thermostable FGF-2 in a particular expression system, e.g., in a prokaryotic expression system (e.g., E. coli) or a mammalian expression system (e.g., CHO cells) based on well known codon usage preferences in various expression systems. In addition, other elements useful in recombinant DNA and expression technology, such as promoters, termination signals, secretion signals, and the like, suitable for a preferred expression system may also be included in the nucleic acid sequence. In addition, all nucleic acid sequences described and claimed herein include the complement of the sequence. In some embodiments, a nucleic acid encoding a thermostable FGF-2 contains the nucleic acid sequence of SEQ ID NO:4, as follows:

```
SEQ ID NO: 4:
ATGGCGGCGGGCAGCATTACCACCCTGCCGGCGCTGCCGGAAGATGGCG

GCAGCGGCGCGTTTCCGCCGGGCCATTTTAAAGATCCGAAACGCCTGTA

TTGCAAAAACGGCGGCTTTTTTCTGCGCATTCATCCGGATGGCCGCGTG

GATGGCGTGCGCGAAAAAAGCGATCCGCATATTAAACTGCAGCTGCAGG

CGGAAGAACGCGGCGTGGTGAGCATTAAAGGCGTGTGCGCGAACCGCTA

TCTGGCGATGAAAGAAGATGGCCGCCTGCTGGCGAGCAAATGCGTGACC

GATGAATGCTTTTTTTTTGAACGCCTGGAAAGCAACAACTATAACACCT

ATCGCAGCCGCAAATATACCAGCTGGTATGTGGCGCTGAACCGCACCGG

CCAGTATAAACTGGGCAGCAAAACCGGCCCGGGCCAGAAAGCGATTCTG

TTTCTGCCGATGAGCGCGAAAAGC
```

In some embodiments, the nucleic acids encoding a thermostable FGF-2 are vectors. A vector can contain any of the nucleic acid sequences described herein. In addition, other elements useful in recombinant technology, such as promoters, termination signals, selection cassettes, and the like, suitable for a preferred expression system may also be included in a vector sequence. In some embodiments, the vector sequence contains a nucleic acid sequence encoding a thermostable FGF-2 having the amino acid sequence of SEQ ID NO:2, e.g., the nucleic acid sequence of SEQ ID NO:4. Any suitable techniques, as known in the art, may be used to construct a vector for expression of a thermostable FGF-2.

Also disclosed herein are cells that incorporate one or more of the above-mentioned vectors for expression of a thermostable FGF-2. The cell may be a prokaryotic cell or a eukaryotic cell. In some embodiments, the cell is a prokaryotic cell, e.g., an E coli cell. In other embodiments, the cell is a Chinese hamster ovary (CHO) cell. Methods for incorporation of the vector(s) into the cell, such as transfection, or viral transduction, and stable selection are well established in the art. are given in the Examples.

Methods for purifying a thermostable FGF-2 from recombinant cells, e.g., E.coli, are known in the art as exemplified in, e.g., Wiedlocha et al., Mol. Cell. Biol. 16(1): 270-280 (1996) and herein.

The invention is also directed at a fully-defined medium suitable for culturing human pluripotent stem cells in an undifferentiated state throughout several passages, the medium containing thermostable FGF-2 K128N having enhanced ability to support pluripotency, as described herein. Suitable culture media (buffered to a pH of about 7.4), in addition to a thermostable FGF-2 as described herein, include, at a minimum, water, salts, amino acids, vitamins, a carbon source, insulin, and selenium. Defined culture media supplemented with high concentrations of wild type FGF-2, e.g., 100 ng/ml, that permit the long-term culture of undifferentiated human pluripotent cells are known in the art (e.g., Ludwig et al., Nat. Methods 3:637-646 (2006), incorporated herein by reference as if set forth in its entirety). Such media include, but are not limited to, commercially available media such as Essential 8™ (Life Technologies) described, among other suitable media, in U.S. patent application Ser. Nos. 13/341,059 and 13/204,354; mTeSR™1 and TeSR™2 (Stem-Cell Technologies, Vancouver)

Preferably, FGF-2 protein concentrations sufficient to support pluripotency are lower for thermostable FGF proteins than for wild type FGF proteins. Specifically, an exemplified FGF-2 with one amino acid mutation, K128N relative to SEQ ID NO: 1, creates a thermostable FGF-2 protein that can support self-renewal of human ES and iPS cells at concentrations 4 to 100-fold lower than those ordinarily used for wild type FGF-2 (about 40-100 ng/ml). It is specifically contemplated that the fully-defined medium described herein contains a thermostable FGF-2, e.g., FGF-2 K128N, at a concentration lower than that required of wild type FGF-2 protein, wherein the lower concentration is at least 5% lower than that required of wild type FGF-2 protein, preferably at least 10% lower than that required of wild type FGF-2 protein, more preferably at least 15%, 20%, 30%, 40%, 50%, 60%, 70%, 80%, 90%, 95%, or 99% lower than that required of wild type FGF-2 protein. In some embodiments, the medium contains a thermostable FGF-2 instead of, or in combination with, wild type FGF-2. For example, the medium might may contain 20%, 40%, 60%, 80% or 99% FGF-2 K128N and the balance being wild type FGF-2.

In some embodiments the culture medium suitable for culture of human pluripotent stem cells contains thermostable FGF-2 K128N at a concentration of 40 ng/ml or less, preferably 10 ng/ml or less, 3 ng/ml or less, or 1 ng/ml or less. In some embodiments, FGF-2 (K128N) is included in the suitable culture medium at a concentration of about 10 ng/ml to about 50 ng/ml, 10 ng to about 30 ng/ml, 3 ng/ml to about 10 ng/ml, 1 ng/ml to about 3 ng/ml, or about 0.2 ng/ml to about 1 ng/ml.

In some embodiments, the thermostable FGF-2-containing medium is suitable for use in a method for the derivation of human ES cell lines or for reprogramming of somatic cells.

The invention is also directed to a composition that contains a human pluripotent stem cell, and a medium containing thermostable FGF-2 K128N that is suitable for culturing human pluripotent cells in an undifferentiated state and having enhanced ability to support pluripotency, as described herein.

III. Methods

The invention also provides a method for culturing human pluripotent stem cells in culture (e.g., hES or hiPS cells). In some embodiments, human pluripotent stem cells, such as human embryonic stem cells or human induced pluripotent cells, are cultured in a medium containing a thermostable FGF-2. In some embodiments, the thermostable FGF-2 used in the method includes a K128 substitution. In some embodiments, the thermostable FGF-2 used in the method contains a K128N substitution as shown in SEQ ID NO:2. The medium used in the method can be any medium that supports human pluripotent cells in culture (e.g., Chen et al., Nat. Meth. 8:424-429, 2011 or any of the commercial media mentioned herein). In some embodiments, thermostable FGF-2 is the only FGF-2 used in the medium used in the culturing method, i.e., it is substituted in commercial media that are pre-formulated with wild type FGF-2. In other embodiments, the medium to be used might may contain 20%, 40%, 60%, 80% or 99% thermostable FGF-2 (e.g., thermostable K128N FGF-2) and the balance being wild type FGF-2. Preferably, the medium is fully defined.

In some embodiments of the invention, human pluripotent cells are cultured with FGF-2 K128N at a concentration of 40 ng/ml or less, preferably 10 ng/ml or less, 3 ng/ml or less, or 1 ng/ml or less. It is contemplated that culture conditions including FGF-2 K128N at a concentration of 40 ng/ml or less, preferably 10 ng/ml, 3 ng/ml, or 1 ng/ml or less, are sufficient for maintaining human pluripotent cells and for reprogramming somatic cells into induced human pluripotent cells. In some embodiments, FGF-2 (K128N) is included at a concentration of about 10 ng/ml to about 50 ng/ml, 10 ng to about 30 ng/ml, 3 ng/ml to about 10 ng/ml, 1 ng/ml to about 3 ng/ml, or about 0.2 ng/ml to about 1 ng/ml.

The invention is also directed at a method for reprogramming human somatic cells into human induced pluripotent (iPS) cells in culture. Somatic cells, such as foreskin fibroblast cells, are cultured in a medium containing a thermostable FGF-2, as described herein, e.g., FGF-2 K128N. The medium can be any medium that supports reprogramming of human somatic cells into human pluripotent cells (e.g., Chen et al., Nat. Meth. 8:424-429, 2011). Preferably, the medium is fully defined. Human somatic cells can be reprogrammed using methods known in the art (e.g., Patent Application Publication Nos. 2008/0233610 and 2010/0184227, each incorporated herein by reference in its entirety as if set forth herein. A medium containing thermostable FGF-2 K128N is also anticipated to be suited for use in other reprogramming methods, such as those mentioned below (and, likewise, each incorporated by reference herein in its entirety): Adenoviral vector reprogramming (Zhou and Freed, Stem Cells 27: 2667-2674, 2009); Sendai virus reprogramming (Fusaki et al., Proc Jpn Acad 85: 348-362, 2009); polycistronic minicircle vector reprogramming (Jia et al., Nat Methods 7: 197-199, 2010); piggyBac transposon reprogramming (Woltjen et al., Nature 458: 766-770, 2009; Yusa et al., Nat Methods 6: 363-369, 2009); recombinant proteins for reprogramming (Zhou et al., Cell Stem Cell 4: 381-384, 2009); whole cell extracts isolated from human ES cells (Cho et al., Blood 116: 386-395, 2010) or genetically engineered HEK293 cells (Kim et al., Cell Stem Cell 4: 472-476, 2009); small molecules to replace individual reprogramming factors (Desponts and Ding, Methods Mol Biol 636: 207-218, 2010; Li and Ding, Trends Pharmacol Sci 31: 36-45, 2010). Suitable human somatic cells include, but are not limited to, blood mononuclear cells, skin-derived fibroblasts, and keratinocytes.

Suitable culture media (buffered to a pH of about 7.4), in addition to a thermostable FGF-2 as described herein, include water, salts, amino acids, vitamins, a carbon source, insulin, and selenium.

In exemplary embodiments, pluripotency of cells derived using methods of the invention, pluripotent cells are cultured in a suitable medium containing FGF-2 K128N at a concentration of about 30 ng/ml for at least five passages (~20-30 days). Passaged cells can then be characterized morphologically and genetically to determine whether they exhibit a human pluripotent phenotype (e.g., round shape, large nucleoli and scant cytoplasm) and express at least one pluripotency marker (e.g., OCT4). Other markers of pluripotency (either at the mRNA or protein level) include, but are not limited to, Nanog, Tra181 and SSEA4.

The invention will be more fully understood upon consideration of the following non-limiting Examples. All papers and patents disclosed herein are hereby incorporated by reference as if set forth in their entirety.

EXAMPLES

Example 1

Variable FGF Pathway Activation in Human Pluripotent Stem Cells by FGF Family Members Cell Culture Human ES cells were maintained in specific media on matrigel-coated tissue culture plates essentially as described previously (Ludwig et al., Nat. Meth. 3:637-646, 2006). Cells were passaged with EDTA essentially as described previously (Chen et al., Cell Stem Cell 7:240-248, 2010). Briefly, cells were washed twice with PBS/EDTA medium (0.5 mM EDTA in PBS, osmolarity 340 mOsm), then incubated with PBS/EDTA for 5 minutes at 37° C. The PBS/EDTA was removed, and the cells were washed swiftly with a small volume of medium.

Cell Growth Measurement

Cell growth was analyzed essentially as described previously (Chen et al., Cell Stem Cell 7:240-248, 2010). E8 cell culture medium was used for cell growth experiments (Chen et al., Nat. Meth. 8:424-429, 2011). All experiments were performed in triplicate using 12-well plates. Prior to the addition of cells, 500 µl medium was loaded into each well. Cells were dissociated for 5 minutes or until fully detached from the plate with TrypLE (INVITROGEN), which was subsequently neutralized with equal volumes of media. The cells were counted, washed, and diluted to concentrations of 100,000 to 300,000 cells/ml and 100 µl of the cell solution was added into each well. At various time points, cells were again dissociated with 0.4 ml TrypLE, neutralized with equal volumes of 10% FBS in DMEM, and counted using flow cytometry. Approximately 5000 count-bright beads (INVITROGEN) were added to each sample as an internal control and 200 beads were counted for each sample. For proliferation experiments, media were changed daily up to the day of analysis, and cells were counted as described above.

FGF Expression and Purification

FGF proteins were expressed in ROSETTA™2 (DE3) pLysS cells (NOVAGEN®) using MAGICMEDIA® (INVITROGEN) at 37° C. for 24 hours. FGF proteins were purified essentially as described by Wiedlocha et al., Mol. Cell. Biol. 16(1): 270-280 (1996), incorporated herein by reference as if set forth in its entirety. Briefly, bacterial pellets were sonicated and centrifuged. The clear supernatant was applied to a heparin cartridge (BIO-RAD) equilibrated with 0.5 M NaCl in 20 mM sodium phosphate (pH 7.5)-1 mM EDTA-1 mM dithiothreitol. Fusion proteins were eluted with 1 M NaCl in the same buffer and dialyzed against 20 mM sodium phosphate (pH 8.0)-1 mM EDTA-1 mM dithiothreitol. Subsequently, the fusion proteins were applied to a Q cartridge (BIO-RAD) and eluted with a linear NaCl gradient in the same buffer.

Figure 1B:
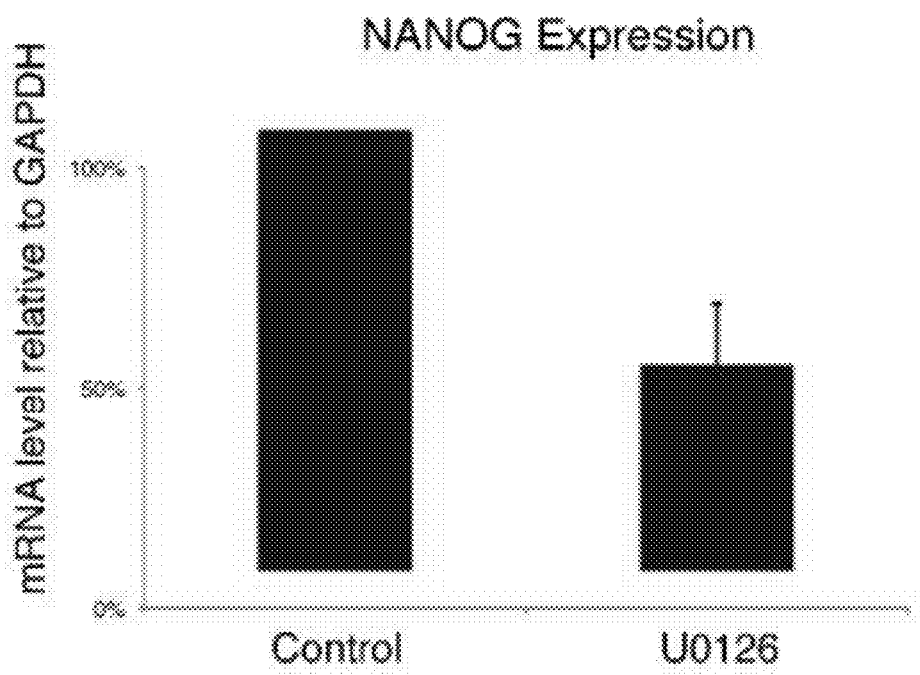
Figures 1C, 1D:
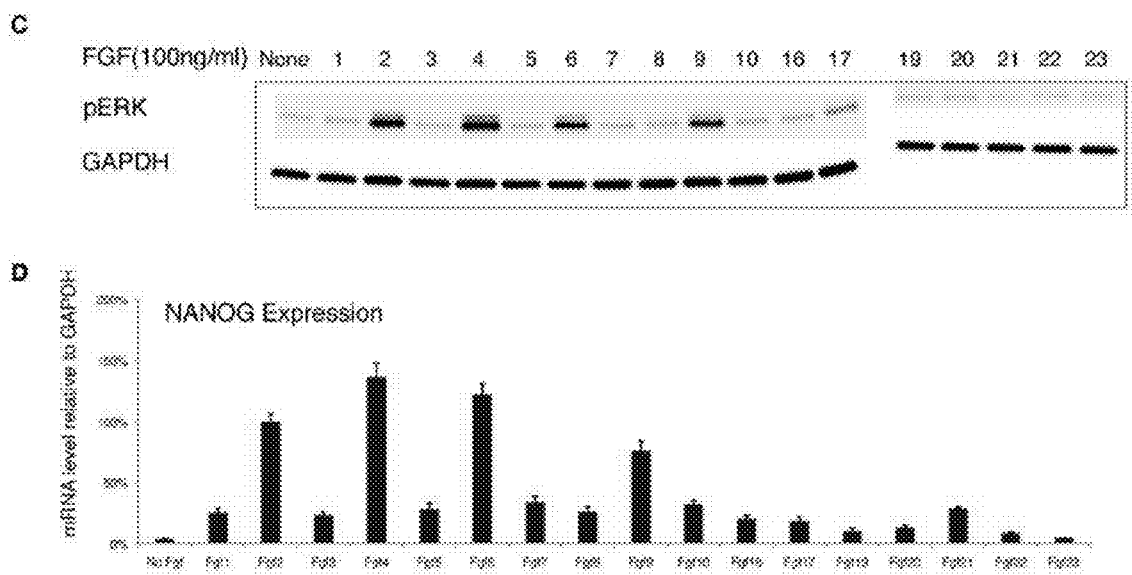
Figure 1E:
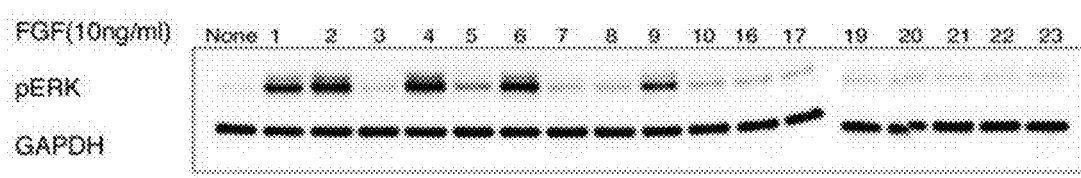
Figure 1F:
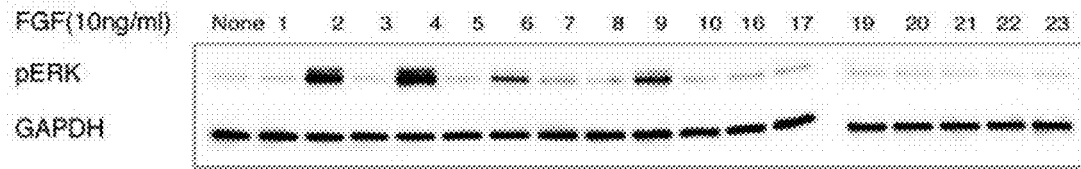
Figures 2A, 2B, 2C:
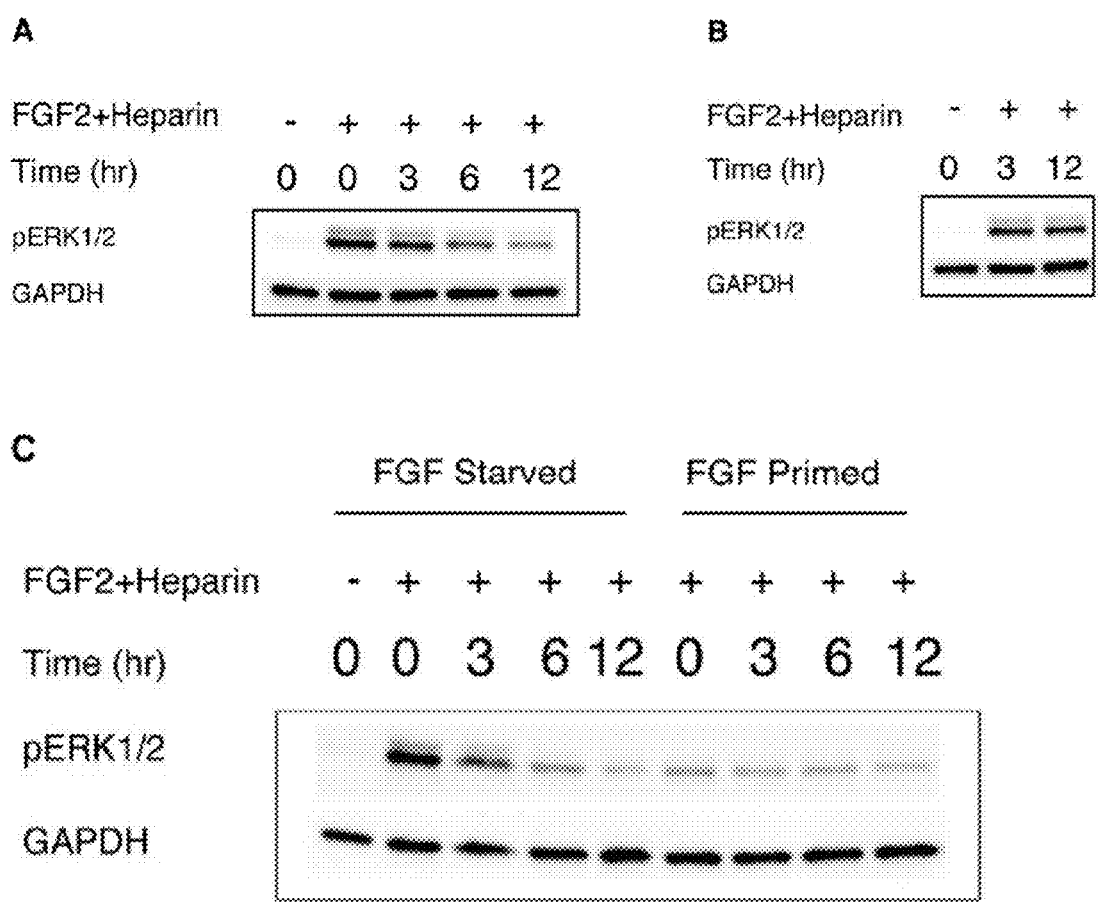
FIG. 2A-C illustrates dynamic regulation to maintain FGF pathway activation at relatively low level.
Figures 3A, 3B, 3C, 3D:
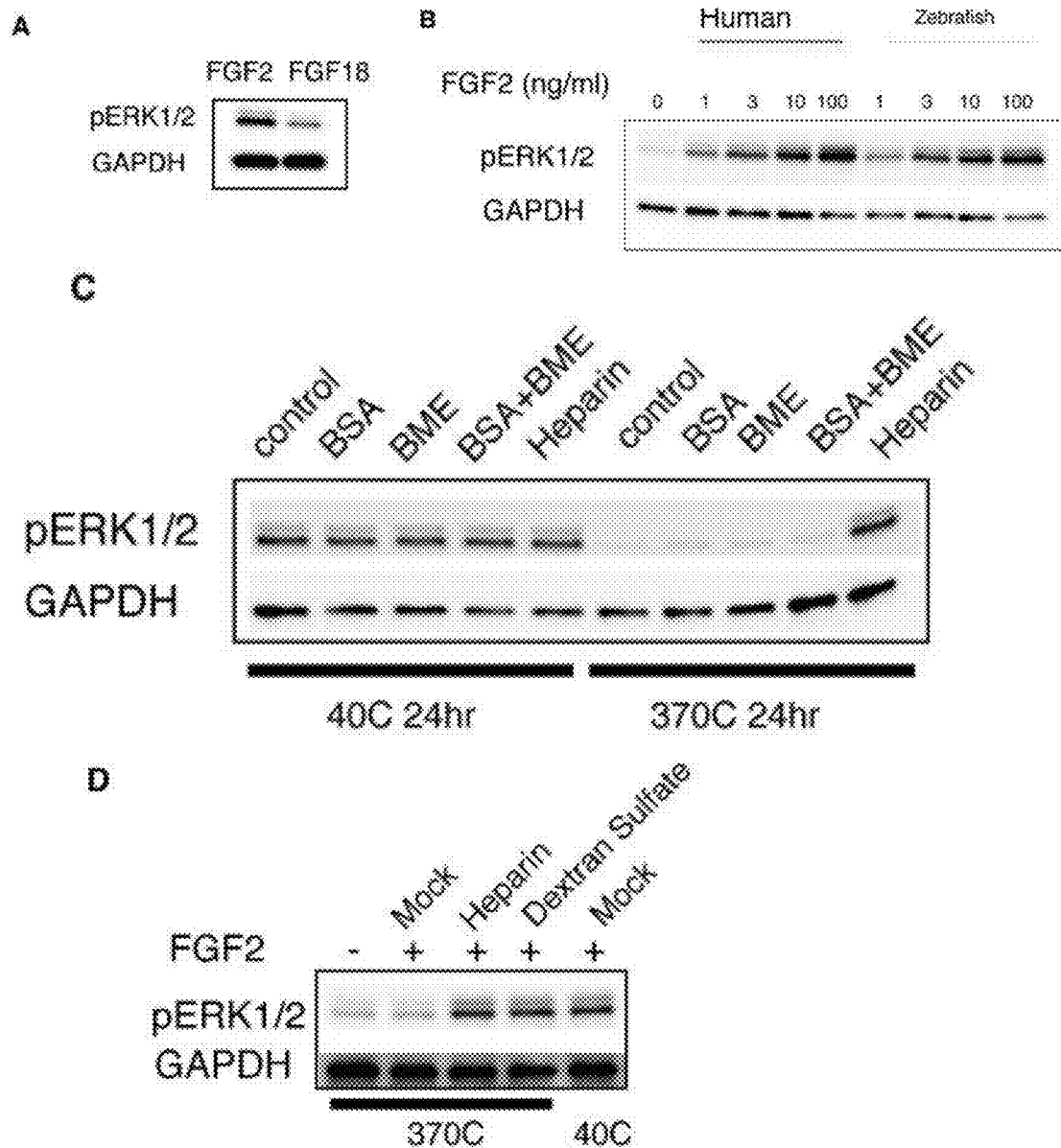
FIG. 3A-G illustrates FGF activity with and without heparin.

Pluripotency of human ES and iPS cells is supported by FGF and TGFβ/NODAL pathways (Vallier et al., J. Cell Sci. 118:4495-4509, 2005). FGF-2, not TGFβ, stimulates MAP kinase ERK1/2 phosphorylation after short-term incubation (15 minutes) (FIG. 1A). At the same time, ERK inhibition suppresses expression of pluripotency marker genes, such as NANOG (FIG. 1B). Cell culture experiments showed that an increase in extracellular signal-regulated kinase (ERK) phosphorylation in human ES cells can be used as reliable indicator of FGF pathway activation. Using ERK phosphorylation and NANOG expression to determine the function of the various FGF family members on human pluripotent stem cells revealed that only FGF-2, FGF-4, FGF-6, and FGF-9 were able to sustain strong ERK phosphorylation after 24 hours in cell culture (FIG. 1C). These results were consistent with NANOG expression in response to the various FGFs in human ES cells (FIG. 1D). However, 15 minute incubations with the various FGF family members led to different ERK phosphorylation patterns (FIG. 1E and FIG. 3A). Strong ERK phosphorylation induced by FGF-1, FGF-2, FGF-4, FGF-6, and FGF-9 correlated with the respective FGF's ability to bind to FGF-1R. FGF-1 lost all ERK phosphorylation activity after 6 hours of 37° C. pre-incubation (FIG. 1F). FGFR downstream ERK phosphorylation decreased gradually after initial induction even when active FGF-2 was still maintained in culture (FIGS. 2A and 2B). In continuous cell culture, ERK phosphorylation was usually maintained at a relatively low level while pluripotency was sustained (FIG. 2C). These results suggest that higher FGF concentrations might not be necessary for stem cells.

Example 2

Wild Type FGF-2 Protein is Thermally Unstable and can be Stabilized by Heparin

Figures 3E, 3F, 3G:
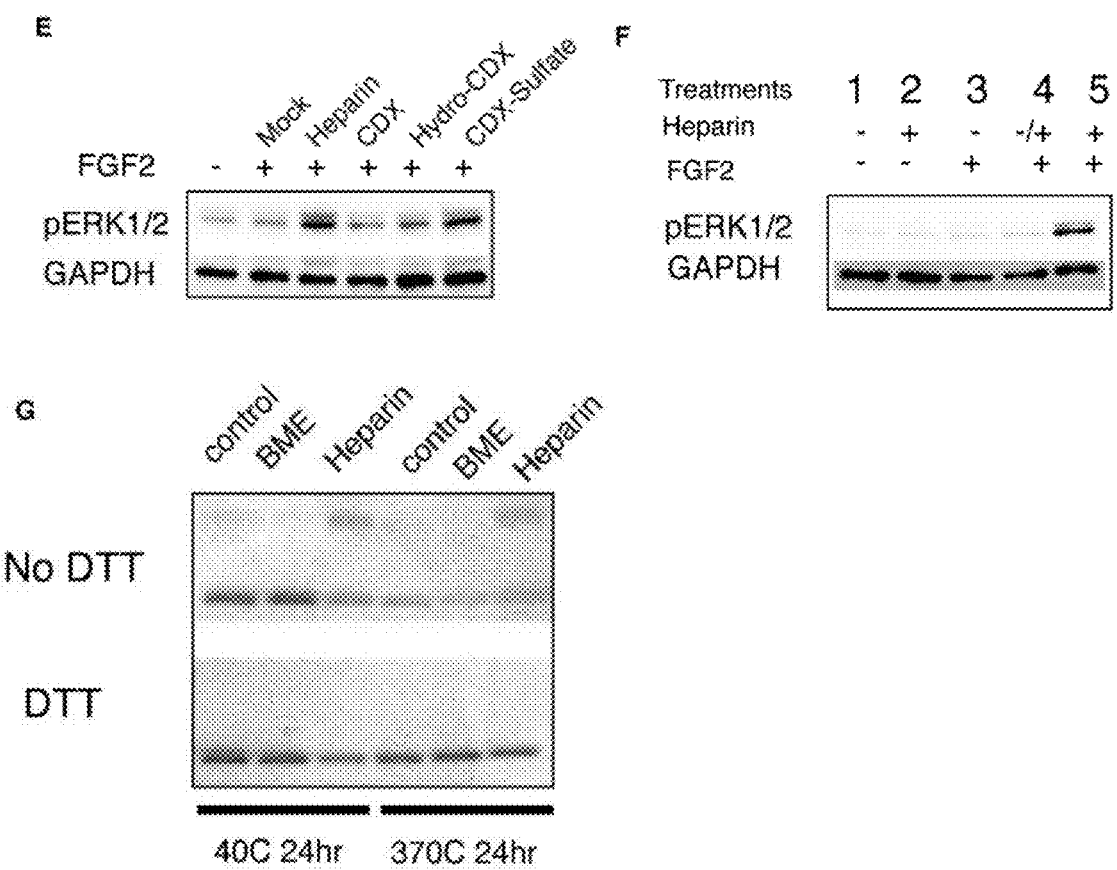
Figure 4A:
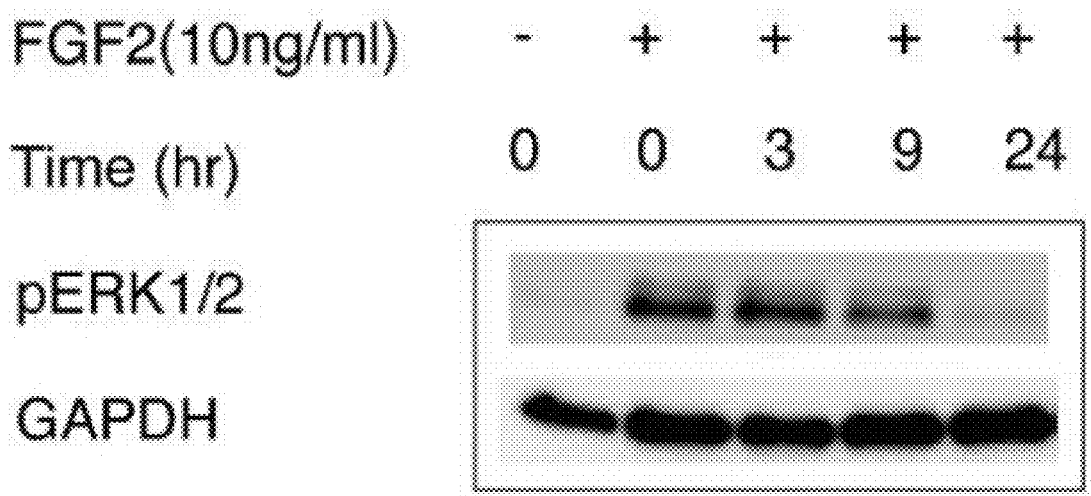
FIG. 4A-D illustrates that loss of FGF-2 activity at 37° C. is rescued by the binding of heparin.
Figure 4B:
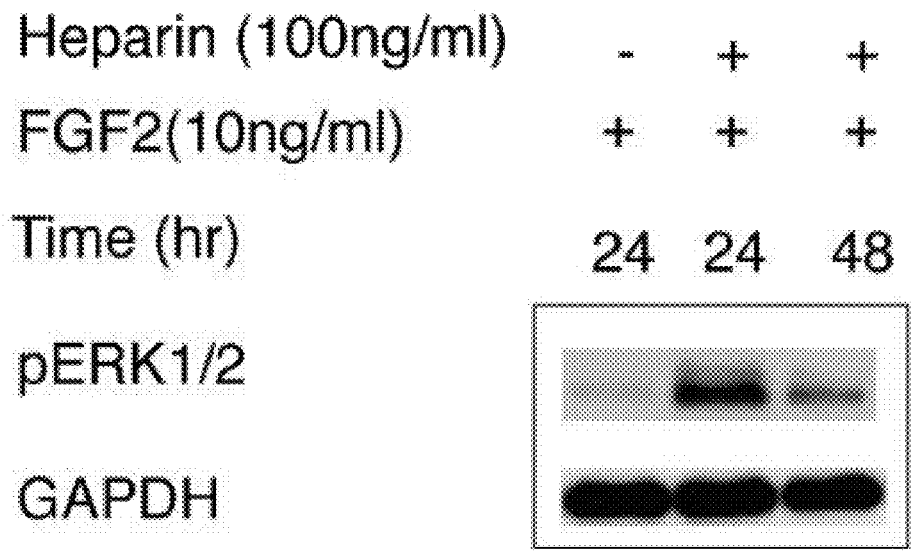

The inventors hypothesized that thermostability of FGF-2 might be associated with the relatively high levels of wild type FGF-2 that are required to maintain pluripotency of human ES cells in culture (e.g., 100 ng/ml). To test this hypothesis, the inventors examined the the FGF-2 proteins most commonly used in hES cell culture, human FGF-2 and zebrafish FGF-2. Both human and zebrafish FGF-2 induce ERK phosphorylation (FIG. 3B) in human ES cells, but both lost most of their activity after 24 hours at 37° C. (FIG. 4A and FIG. 3C). Addition of heparin to the medium maintained the activity of both human and zebrafish FGF-2 proteins (FIG. 4B and FIG. 3C). However, heparin cannot recover FGF activity after the protein is heat-inactivated (FIG. 3D). Several other sulfate-rich polymers preserved FGF-2 activity during incubation (FIGS. 3D and 3E). Co-incubation with BSA or reducing reagents failed to preserve FGF-2 activity (FIG. 3C).

Figure 4C:
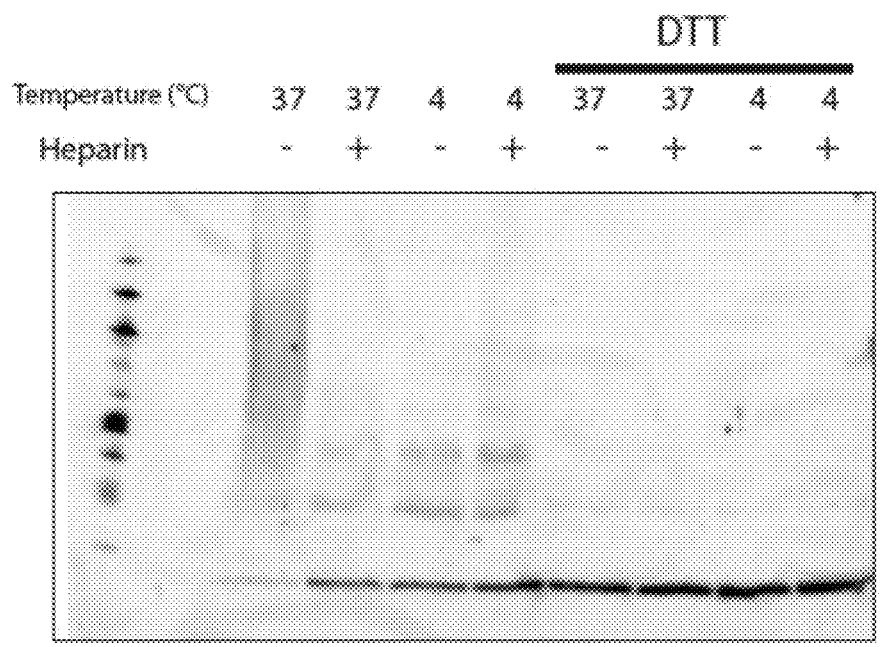
Figure 4D:
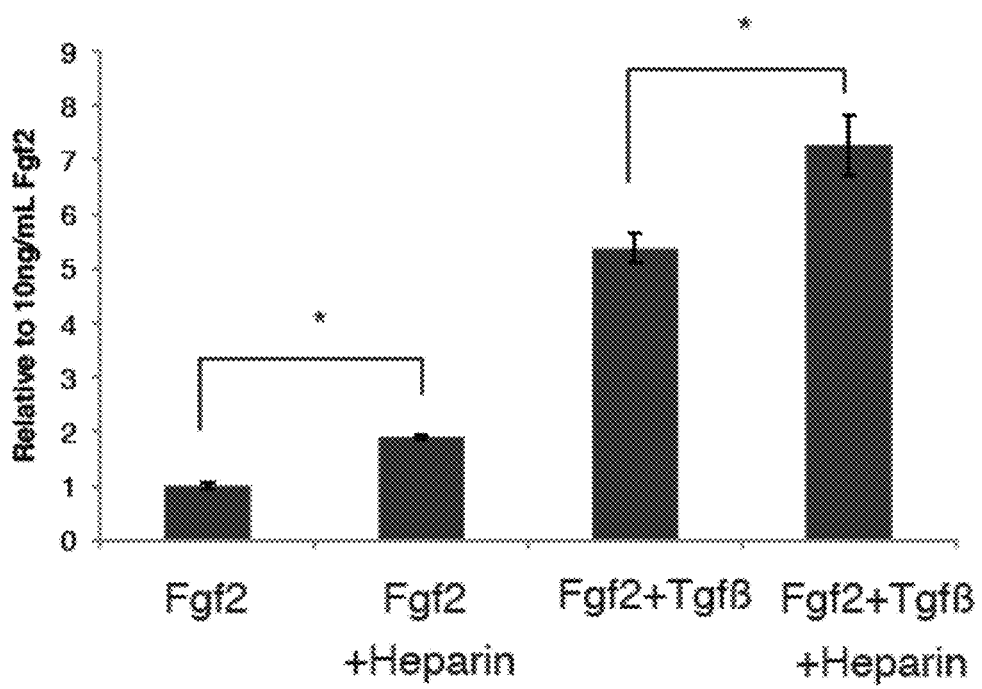

To assess the mechanism of FGF activity loss at 37° C., Western blot analysis was performed. Human and zebrafish FGF-2 formed aggregates after incubation at 37° C. (FIGS. 4C and 3E). Heparin prevented heat-induced aggregation (FIG. 4C). It was previously thought that heparin helps stimulate the FGF- or other pathways. The results presented herein provided an alternative function of heparin in cell culture, i.e., maintaining FGF-2 stability and preventing aggregation. Prevention of heat-induced aggregation explains, at least in part, heparin's ability to promote pluripotency (FIG. 4D). Heparin's role in maintaining FGF-2 was consistent with its ability to improve the expression of pluripotency markers, such as NANOG (FIG. 4D).

Example 3

FGF-2 K128N has Reduced Affinity for Heparin and is Thermally Stable

The inventors found that mutating the heparin-binding site of FGF-1 (K112N) stabilizes FGF1 WT and FGF1 3X. Thus, the inventors hypothesized that mutating FGF-2 at the conserved heparin-binding site (K128) could potentially stabilize FGF-2 as well.

Figure 5:
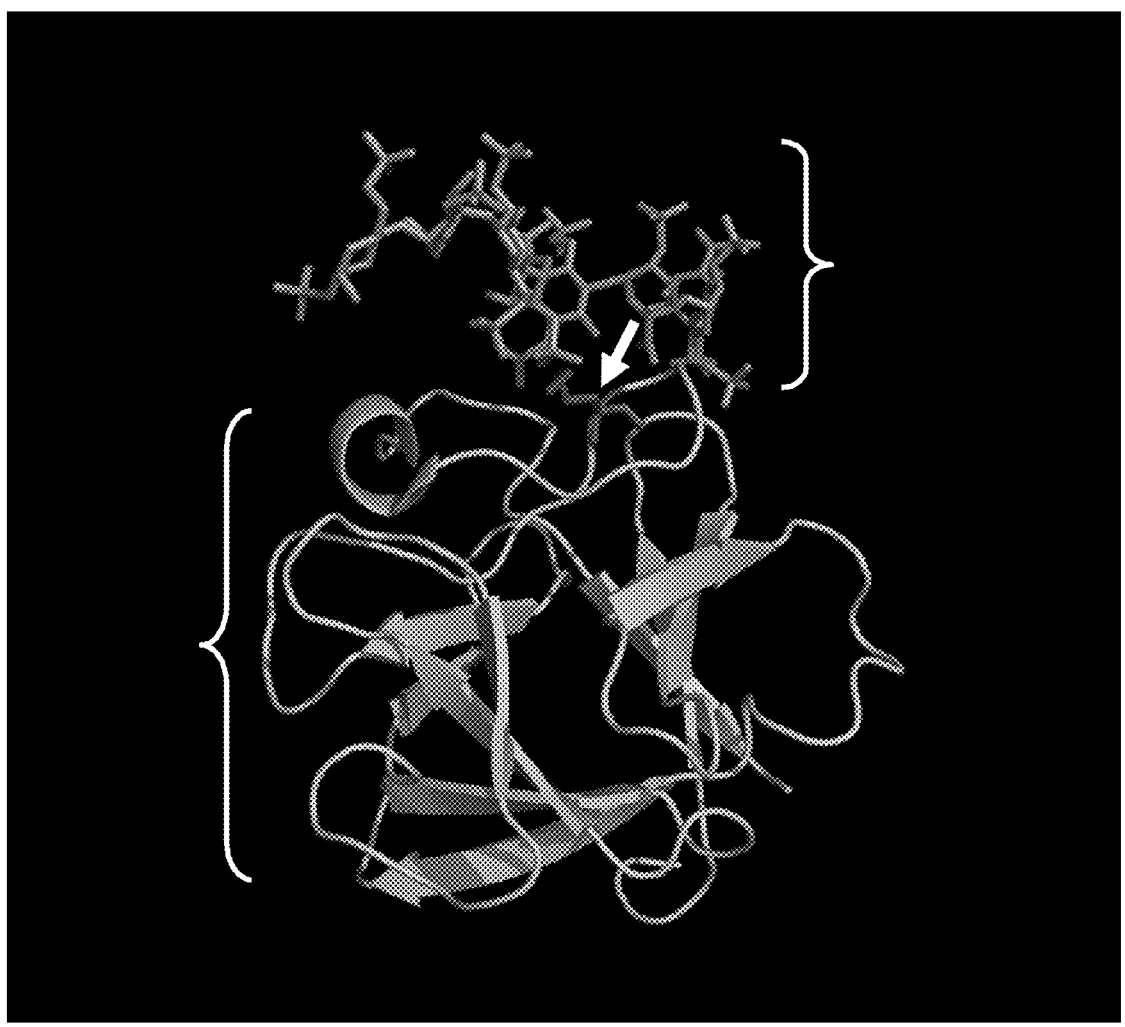
FIG. 5 illustrates the position of K128 in human FGF-2 protein relative to heparin. FGF-2 is indicated by bottom left bracket. Heparin is indicated by top right bracket. Amino acid K128 is indicated by an arrow. Molecular structure was generated using PyMol, PDB file 1FQ9.

To predict what substitution mutation at K128 might stabilize FGF-2, the inventors determined the molecular structure of FGF-2 relative to heparin (FIG. 5) and predicted that substituting K128 with N would decrease the affinity of FGF-2 for heparin. There was no previous report on this mutation, so the inventors generated FGF-2 (K128N) as previously described (Schlessinger et al., Mol. Cell. 6:743-750 (2000)).

Figure 6:
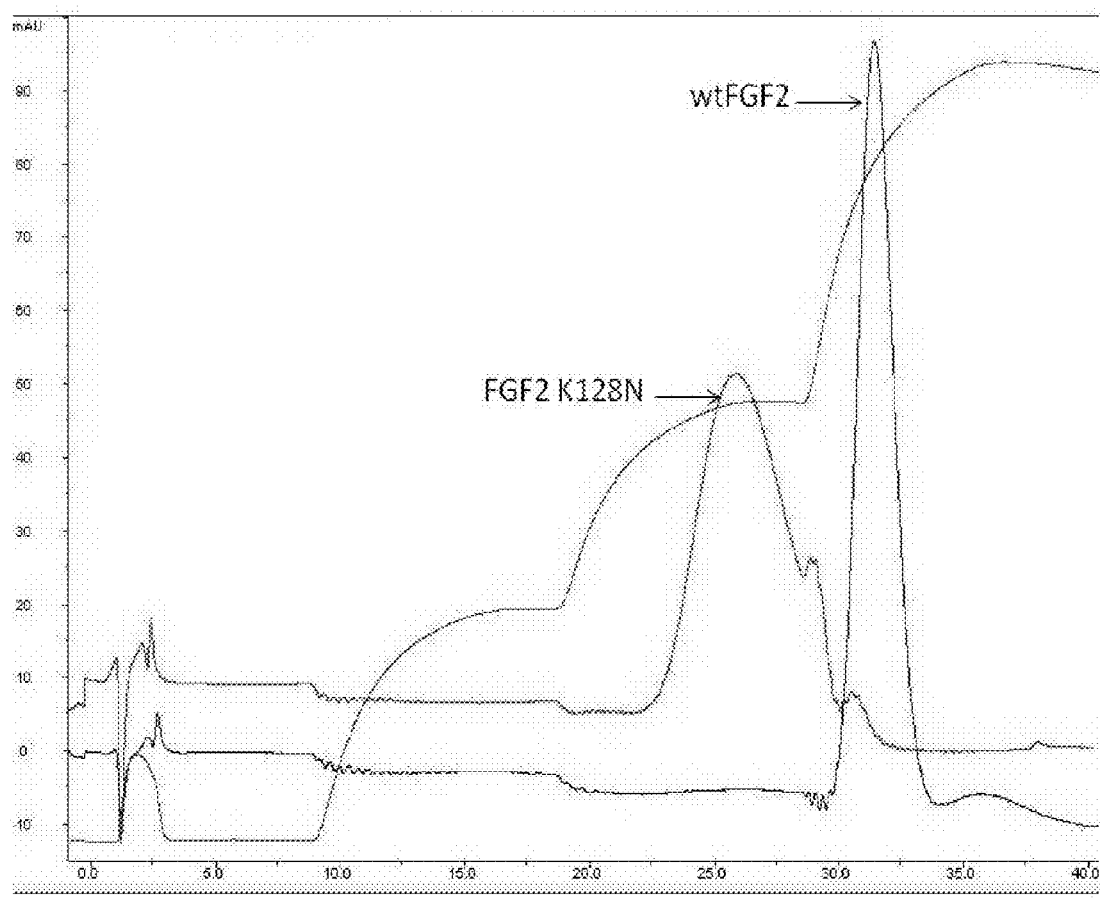
FIG. 6 illustrates an overlay elution profile of wild type FGF-2 and FGF-2 K128N, showing that a K128N substitution decreases FGF-2's affinity for heparin.

To measure FGF-2 K128N's affinity for heparin relative to wild type FGF-2, wild type FGF-2 or FGF-2 K128N were loaded separately onto HiTrap Heparin columns in PBS and eluted with 0.5M, 1M, 2M NaCl step gradient in PBS. The majority of FGF-2 K128N was eluted in 1M NaCl and wild type FGF-2 was eluted only in 2M NaCl (FIG. 6). The elution profile of wild type FGF-2 and FGF-2 K128N shows that a K128N substitution decreases FGF-2's affinity for heparin. Mutant FGF-2 K128N still has some affinity to heparin because K128 is not the only amino acid residue making contact with heparin.

Figure 7A:
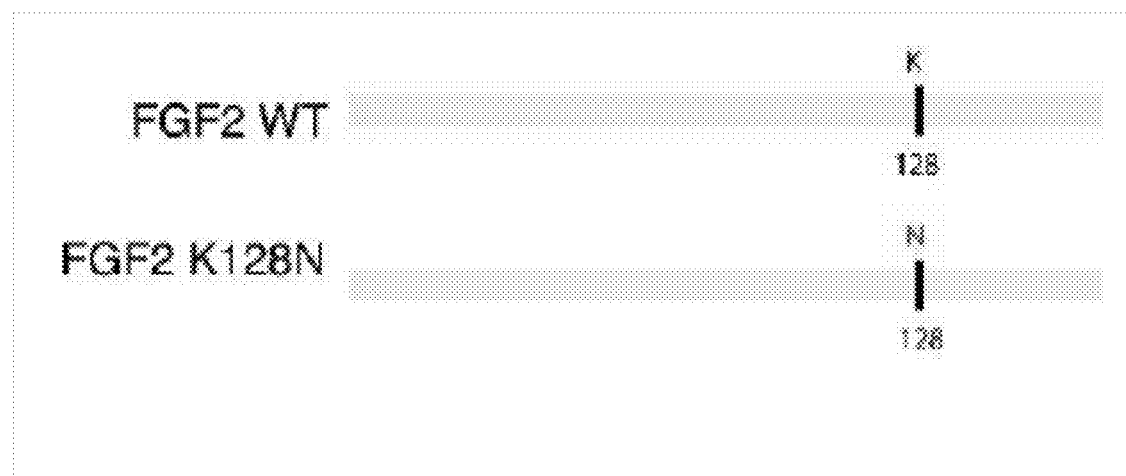
FIG. 7A-B illustrates stabilized FGF-2 proteins.
Figure 7B:
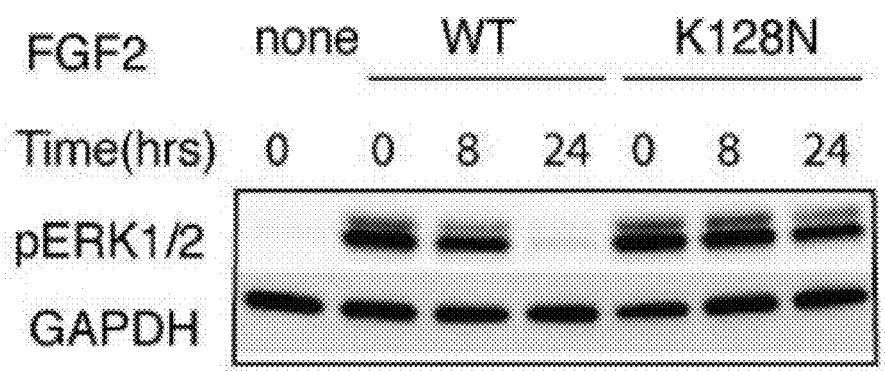

To determine thermal stability of FGF-2 K128N relative to wild type FGF-2 phosphorylation of ERK kinase, a downstream effector of FGF pathway, was measured. Wild type FGF-2 and FGF2-K128N proteins were first incubated in E8 medium at 37° C. and then, at a specific time point, the FGF-2 incubated medium was applied to FGF-starved human ES cells for a period of 15 minutes. Protein from this cell culture was then harvested to measure phosphorylation of ERK kinase. Wild type FGF-2 is not stable at 37° C. (FIG. 7B). However, mutating FGF-2 at K128N led to stable FGF-2 at 37° C. (FIG. 7B).

Example 4

Thermostable FGF-2 Supports Pluripotency of Human ES Cells in vitro

To determine if a low concentration of FGF-2 K128N could support pluripotency of hES cells in vitro relative to wild type FGF-2 hES cells were cultured using various media.

Figure 8:
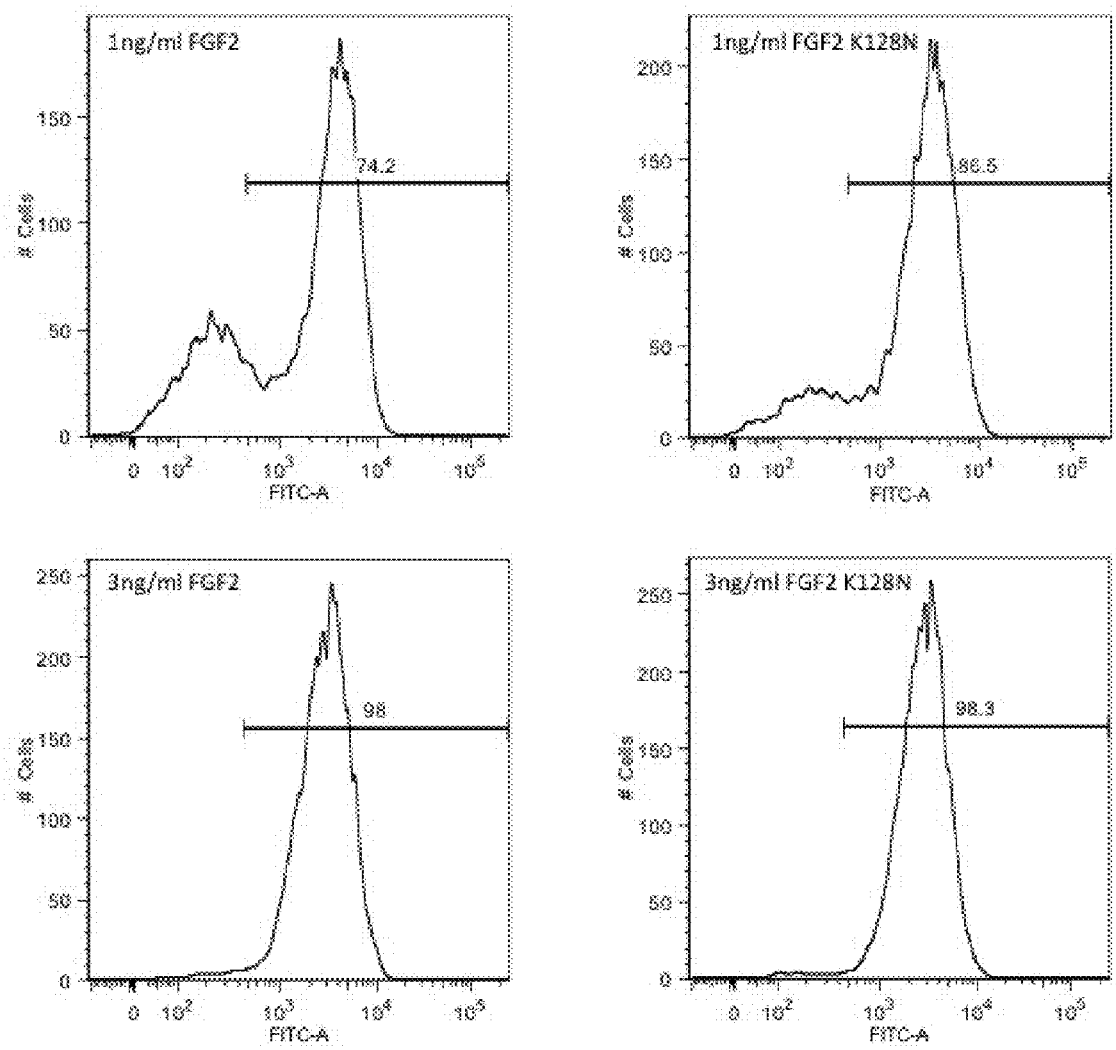
FIG. 8 illustrates maintenance of hES cells with media containing low concentrations of FGF-2 K128N relative to wild type FGF-2. Human H1 ES cells were cultured in E8 media (with TGFbeta1) with different concentrations of either FGF-2 or FGF-2 K128N for 10 passages. Cells were harvested and stained for OCT4. Percentage of OCT4 positive cells is shown in each plot.

H1 hES cells were cultured in E8 medium (with TGFbeta1) with different concentrations (i.e., 1 ng/ml or 3 ng/ml) of either FGF-2 or FGF-2 K128N for 10 passages. Cells were harvested and stained for OCT4, a pluripotency marker. The number of OCT4 positive cells generated under these culture conditions illustrates that pluripotency of hES cells is maintained during culture with low concentrations of FGF-2 K128N relative to wild type FGF-2 (FIG. 8). One ng/ml and 3 ng/ml FGF2-K128N were sufficient to maintain H1 human ES cells with >93% OCT4-positive staining after 10 passages with normal karyotypes.

Figure 9A:
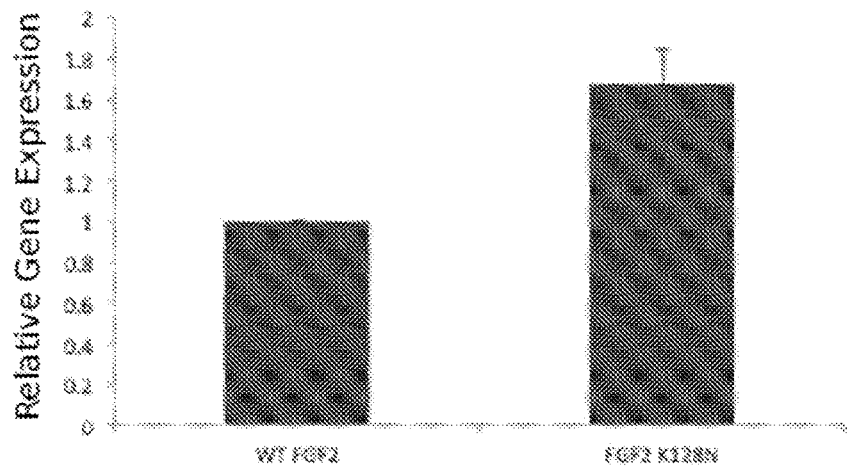
FIG. 9A-C illustrates maintenance of hES cells with media containing low concentrations of FGF-2 K128N relative to wild type FGF-2.
Figure 9A:
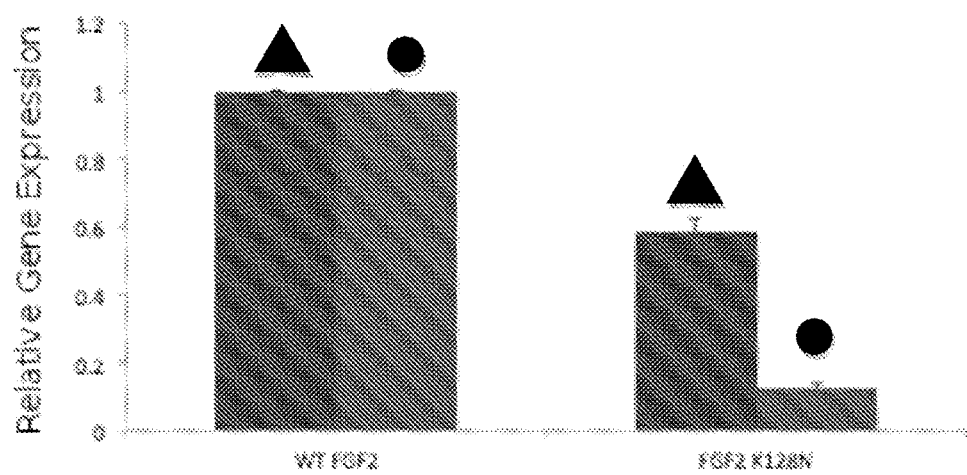
Figure 9B:
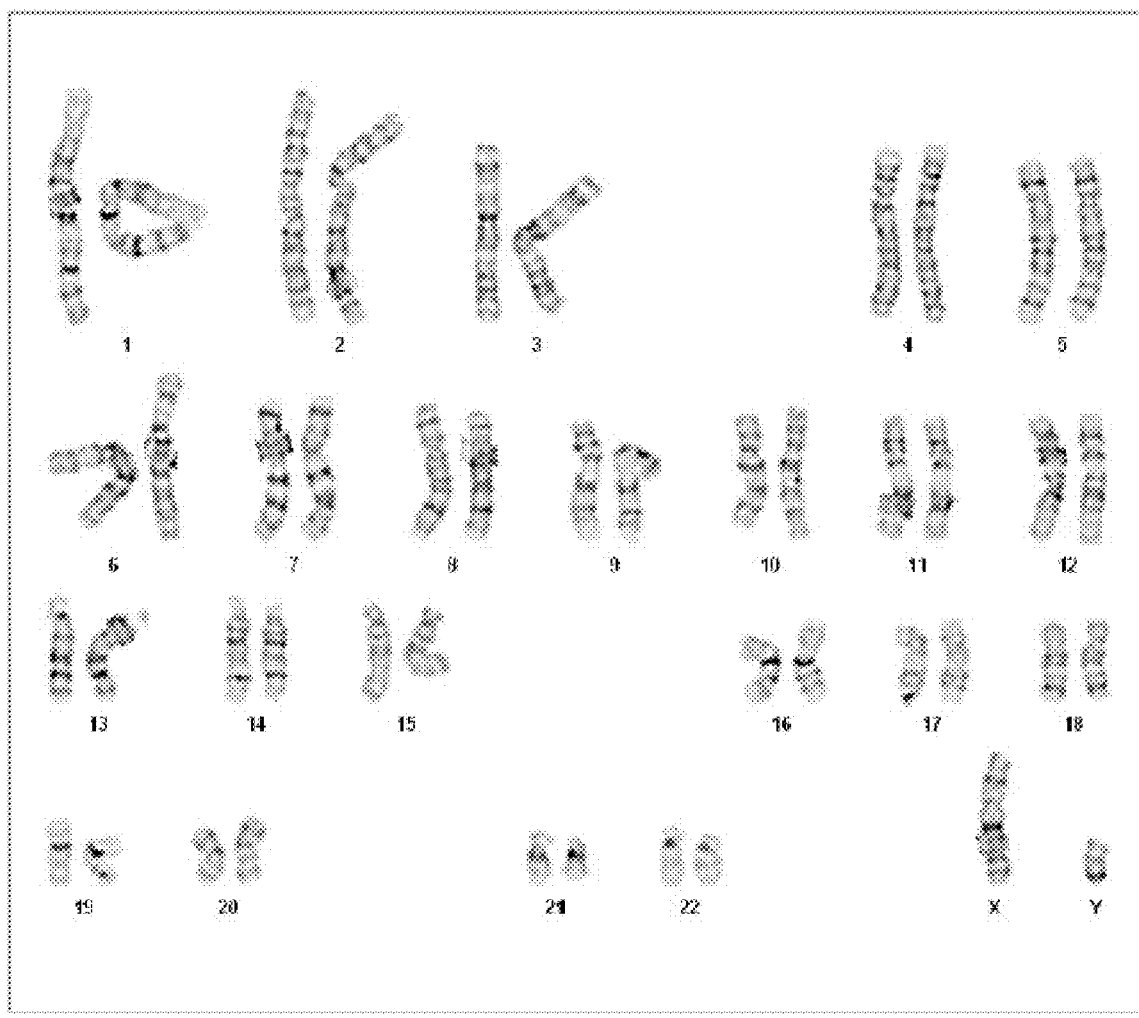
Figure 9C:
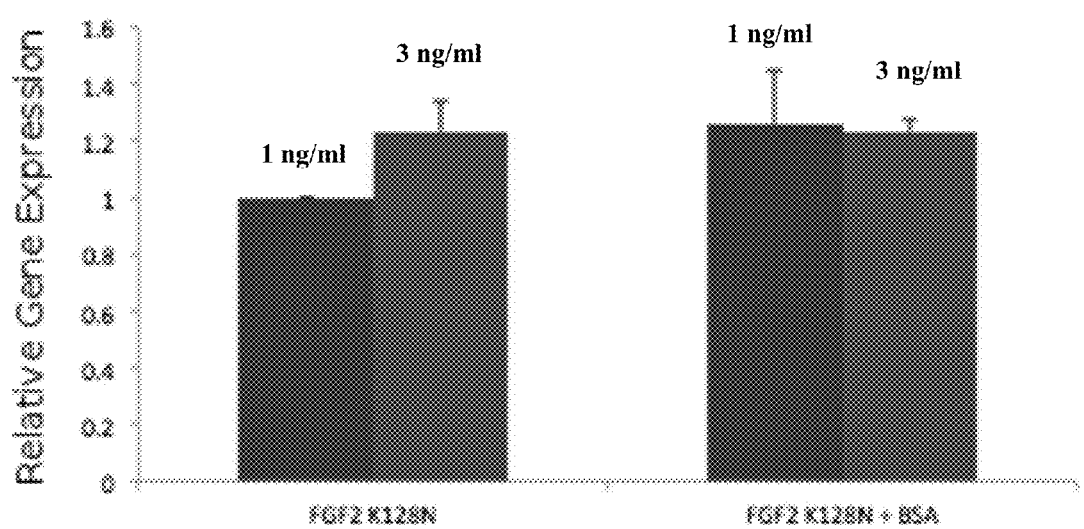

In further experiments, human H1 human ES cells were cultured in E8 (TGF-Beta1) with different FGF proteins at 1 ng/ml. Cells were passaged every 3-4 days, when cells reached ~60% confluency. Following 6 passages, RNA was harvested for RT-qPCR. Following 10 passages, cell karyotypes were tested. Expression of the pluripotency marker Nanog was significantly higher in FGF-2 K128N-cultured cells relative to cells cultured with wildtype FGF-2 (FIG. 9A). Expression of the differentiation markers HAND1 (left) and GATA2 (right) was lower in FGF-2 K128N-cultured cells relative to cells cultured with wild type FGF-2 (FIG. 9A). Cell karyotypes were normal (FIG. 9B). These data suggest that maintenance of human pluripotent stem cells is increased by culturing them with 1 ng/ml FGF-2 K128N relative to culturing with wild type FGF-2.

Plastic ware, including dishes typically used for cell culture, can adsorb proteins such as FGF-2 (Chen et al., Nat. Meth. 8:424-429, 2011) and thus can significantly decrease growth factor activity in the culture. This effect is especially evident when growth factors are used at low concentrations. To determine if the effect of plastic ware adsorption can be overcome, the inventors cultured human H1 human ES cells in E8 (TGF-Beta1) with different FGF proteins at 1 ng/ml (left bar) or 3 ng/ml (right bar) with or without the blocking reagent bovine serum albumin (BSA). Cells were passaged every 3-4 days when cells reached ~60% confluency. Following 6 passages, RNA was harvested for RT-qPCR. Culture with the blocking reagent BSA significantly improved cellular NANOG expression when cells were cultured with FGF2-K128N at 1 ng/ml but not at 3 ng/ml (FIG. 9B). These results suggest that at 3 ng/ml FGF2-K128N can efficiently support human ESC/iPSC pluripotency, taking into account the effect of plastic ware adsorbance of growth factors.

Example 5

FGF-2 Stability Affects Reprogramming of Somatic Cells to Human Pluripotent Stem Cells To determine if FGF-2 thermostability affects reprogramming, foreskin fibroblast cells were reprogrammed as previously described using FGF-2 K128N (5 ng/ml) to replace wild type FGF-2 in culture media at each reprogramming stage (Chen et al., Nat. Meth. 8:424-429, 2011).

Figure 10:
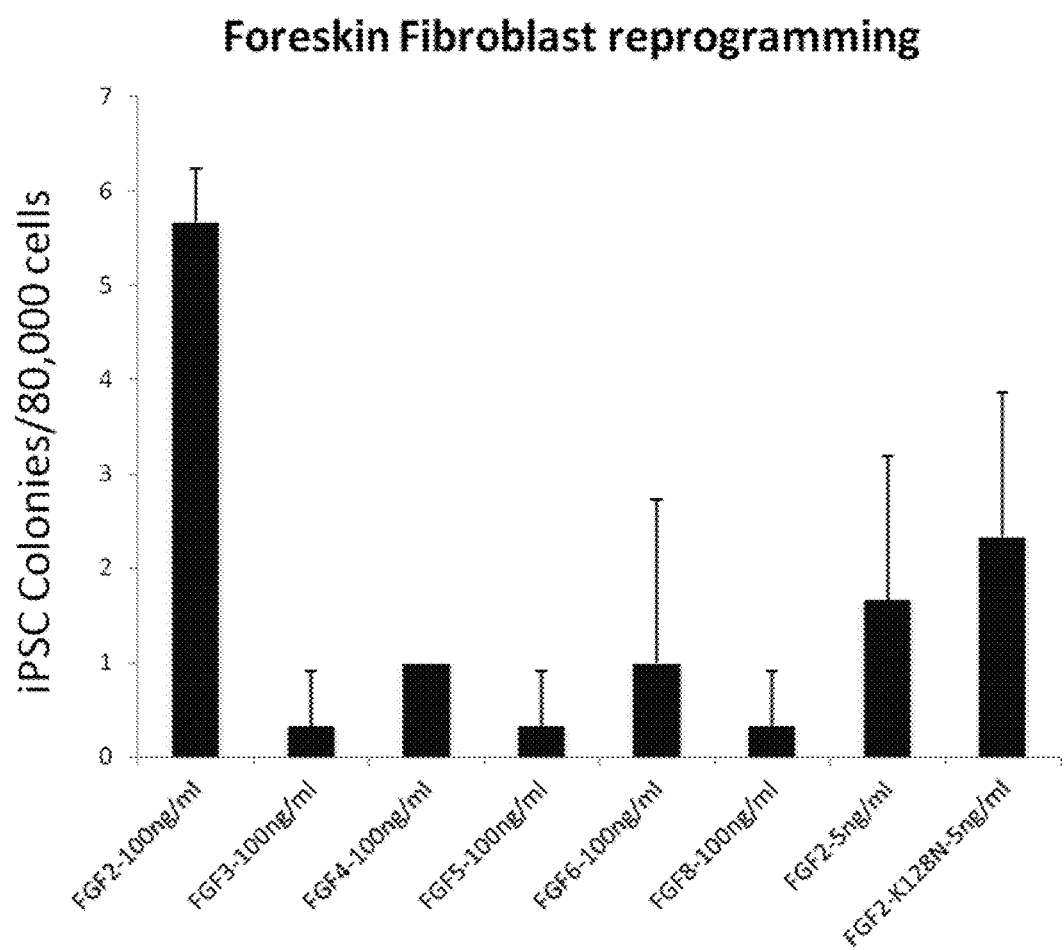
FIG. 10 illustrates that culture with FGF-2 K128N permits reprogramming of foreskin fibroblast cells into iPS cells.

Thermostable FGF-2 K128N is sufficient to replace wild type FGF-2 in reprogramming of foreskin fibroblasts into iPS cells (FIG. 10).

Example 6

Low Levels of FGF-2 K128D Relative to Wild Type FGF-2 do not Support Pluripotency of Human Cells in vitro Two experiments were performed using FGF-2 K128D for the maintenance of hiPS cells in both TeSR and E8 media. The first experiment utilized FGF-2 K128D made by Cellular Dynamics International (CDI), with experimental conditions at 10, 30, 50 and 100 ng/mL with 100 ng/mL zebrafish bFGF as a control. In the second experiment, FGF-2 K128D manufactured by Aldevron was used, with experimental conditions at 30 ng/mL with 100 ng/mL zebrafish bFGF as a control. Conditions were assayed by flow cytometry for the pluripotency markers Oct4, Tra181 and SSEA4 at P0 and P5. Criteria for "human pluripotent" are >90% Oct4 expression and >80% Tra181 and SSEA4 expression.

TeSR culture conditions: Human iPS cells were cultured on Matrigel-coated tissue culture plates in mTeSR1 using standard techniques. Cells were cultured for five passages using normal Dispase splitting.

E8 culture conditions: Human iPS cells were cultured on Matrigel-coated tissue culture plates in E8 using standard techniques. Cells were cultured for five passages using EDTA splitting. Briefly, cells were washed twice with PBS, then incubated with 0.5 mM EDTA for 8 minutes at room temperature. The EDTA was removed, and the cells were washed swiftly with a small volume of medium.

FGF-2 K128D produced at CDI supported pluripotency of hiPSC for five passages in both TeSR and E8 at 100 ng/mL but failed to support pluripotency of hiPSC for five passages in both TeSR and E8 at 50-, 30-, or 10 ng/mL (FIG. 11A). FGF-2 K128D manufactured by Aldevron supported pluripotency of two hiPS cell lines for five passages in TeSR, but failed to support pluripotency of the same two cell lines when cultured in E8 medium at 30 ng/mL. FGF-2 K128N was sufficient to support pluripotency of hiPS cells at 30 ng/ml in either TeSR or E8 medium (FIG. 11C). Three experiments were performed using FGF-2 K128N for the maintenance of hiPSC in both TeSR and E8. The first experiment utilized FGF-2 K128N produced at CDI, with experimental conditions at 5, 15, and 30 ng/mL with 100 ng/mL zebrafish bFGF as a control. In the second and third experiments, FGF-2 K128N manufactured by Aldevron was used, with experimental conditions at 5, 15, and 30 ng/mL with 100 ng/mL zebrafish bFGF as a control. The criteria for pluripotency were as above.

SEQUENCES

SEQ ID NO: 1. Amino acid sequence of wild type human FGF-2 isoform 3.
MAAGSITTLPALPEDGGSGAFPPGHFKDPKRLYCKNGGFFLRIHPDGRVDGVREKSDPHI
KLQLQAEERGVVSIKGVCANRYLAMKEDGRLLASKCVTDECFFFERLESNNYNTYRSR
KYTSWYVALKRTGQYKLGSKTGPGQKAILFLPMSAKS SEQ ID NO: 2. Amino acid sequence of thermostable FGF-2 K128N
MAAGSITTLPALPEDGGSGAFPPGHFKDPKRLYCKNGGFFLRIHPDGRVDGVREKSDPHI
KLQLQAEERGVVSIKGVCANRYLAMKEDGRLLASKCVTDECFFFERLESNNYNTYRSR
KYTSWYVALNRTGQYKLGSKTGPGQKAILFLPMSAKS SEQ ID NO: 3. Amino acid sequence of FGF-2 K128D relative to wild type FGF-2.
MAAGSITTLPALPEDGGSGAFPPGHFKDPKRLYCKNGGFFLRIHPDGRVDGVREKSDPHI
KLQLQAEERGVVSIKGVCANRYLAMKEDGRLLASKCVTDECFFFERLESNNYNTYRSR
KYTSWYVALDRTGQYKLGSKTGPGQKAILFLPMSAKS

```
                                SEQUENCES

SEQ ID NO: 4: Nucleic acid sequence encoding the amino acid sequence shown for
SEQ ID NO: 2.
ATGGCGGCGGGCAGCATTACCACCCTGCCGGCGCTGCCGGAAGATGGCGGCAGCGG
CGCGTTTCCGCCGGGCCATTTTAAAGATCCGAAACGCCTGTATTGCAAAAACGGCGG
CTTTTTTCTGCGCATTCATCCGGATGGCCGCGTGGATGGCGTGCGCGAAAAAAGCGA
TCCGCATATTAAACTGCAGCTGCAGGCGGAAGAACGCGGCGTGGTGAGCATTAAAG
GCGTGTGCGCGAACCGCTATCTGGCGATGAAAGAAGATGGCCGCCTGCTGGCGAGC
AAATGCGTGACCGATGAATGCTTTTTTTTTGAACGCCTGGAAAGCAACAACTATAAC
ACCTATCGCAGCCGCAAATATACCAGCTGGTATGTGGCGCTGAACCGCACCGGCCA
GTATAAACTGGGCAGCAAAACCGGCCCGGGCCAGAAAGCGATTCTGTTTCTGCCGA
TGAGCGCGAAAAGC
```

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. An isolated fibroblast growth factor-two, FGF-2, polypeptide, as depicted in SEQ ID NO: 2, that differs from wild type FGF-2, as depicted in SEQ ID NO: 1, at amino acid position 128, wherein the isolated FGF-2 contains an asparagine submitted for lysine at position 128 (a K128N substitution).

2. An isolated nucleic acid encoding the isolated FGF-2 of claim 1.

3. An isolated genetically modified cell producing the isolated fibroblast growth factor of claim 1.

4. A method for culturing human pluripotent stem cells, the method comprising the step of culturing a human pluripotent stem cell in a medium comprising a K128-substituted thermostable fibroblast growth factor-two, FGF-2, as depicted in SEQ ID NO: 2, that differs from wild type FGF-2, as depicted in SEQ ID NO: 1, at position 128 of the wild type FGF-2, wherein the thermostable FGF-2 contains an asparagine submitted for lysine at position 128 (a K128N substitution).

5. The method of claim 4, wherein the human pluripotent cells are selected from the group consisting of human embryonic stem cells and human induced pluripotent stem cells.

6. The method of claim 4, wherein the medium further comprises heparin.

7. The method of claim 4, wherein the medium comprises the thermostable FGF-2 at a concentration of less than 40 ng/ml.

8. The method of claim 7, wherein the medium comprises the thermostable FGF-2 at a concentration less than 10 ng/ml.

9. The method of claim 8, wherein the medium comprises the thermostable FGF-2 at a concentration less than 3 ng/ml.

10. The method of claim 9, wherein the medium comprises a thermostable FGF-2 at a concentration less than 1 ng/ml.

11. A fully defined culture medium suitable for culturing human pluripotent cells in an undifferentiated state, the medium comprising thermostable fibroblast growth factor-two, FGF-2, as depicted in SEQ ID NO:2, that differs from wild type FGF-2, as depicted in SEQ ID NO: 1, at amino acid 128 of the wild type FGF-2, wherein the thermostable FGF-2 contains an asparagine submitted for lysine at position 128 (a K128N substitution).

12. The fully-defined medium of claim 11, wherein the fully defined medium comprises thermostable FGF-2 at less than 40 ng/ml.

13. The fully-defined medium of claim 12, wherein the fully defined medium comprises thermostable FGF-2 at less than 10 ng/ml.

14. The fully-defined medium of claim 13, wherein the fully medium comprises thermostable FGF-2 at less than 3 ng/ml.

15. The fully-defined medium of claim 14, wherein the concentration of the thermostable FGF-2 in the fully defined medium is equal to or less than 1 ng/ml.

16. A composition comprising:
    a human pluripotent stem cell;
    a medium suitable for culturing the human pluripotent cell in an undifferentiated state; and
    a thermostable fibroblast growth factor-two, FGF-2, as depicted in SEQ ID NO:2, that differs from wild type FGF-2, as depicted in SEQ ID NO: 1, at amino acid 128 of the wild type FGF-2, wherein the thermostable FGF-2 contains an asparagine submitted for lysine at position 128 (a K128N substitution).

17. The composition of claim 16, wherein the medium comprises thermostable FGF-2 at less than 40 ng/ml.

18. The composition of claim 17, wherein the medium comprises thermostable FGF-2 at less than 10 ng/ml.

19. The composition of claim 18, wherein the medium comprises thermostable FGF-2 at less than 3 ng/ml.

20. The composition of claim 19, wherein the medium comprises thermostable FGF-2 at less than 1 ng/ml 1.

21. A method for culturing reprogrammed human somatic cells comprising:
    culturing reprogrammed human somatic cells in a medium until they express markers indicative of induced pluripotent stem cells, wherein the medium comprises water, salts, amino acids, vitamins, a carbon source, insulin, selenium and thermostable fibroblast growth factor-two, FGF-2, as depicted in SEQ ID NO:2, that differs from wild type FGF-2, as depicted in SEQ ID NO: 1, at amino acid 128 of the wild type FGF-2, wherein the thermostable FGF-2 contains an asparagine submitted for lysine at position 128 (a K128N substitution).

22. The method of claim 21, wherein the medium comprises thermostable FGF-2 at less than 40 ng/ml.

23. The method of claim 22, wherein the medium comprises thermostable FGF-2 at less than 10 ng/ml.

24. The method of claim 23, wherein the medium comprises thermostable FGF-2 at less than 3 ng/ml.

25. The method of claim 22, wherein the medium comprises thermostable FGF-2 at less than 1 ng/ml.

26. The method of claim 21, wherein the medium is serum-free.

* * * * *